United States Patent [19]

Kitaura et al.

[11] 4,354,966
[45] Oct. 19, 1982

[54] PEPTIDES, PROCESS FOR PREPARATION THEREOF AND USE THEREOF

[75] Inventors: Yoshihiko Kitaura, Sakurai; Osamu Nakaguchi, Toyonaka; Keiji Hemmi; Matsuhiko Aratani, both of Suita; Hidekazu Takeno, Tenri; Satoshi Okada, Takatsuki; Hirokazu Tanaka; Masashi Hashimoto, both of Takarazuka, all of Japan

[73] Assignee: Fujisawa Pharmaceutical Co., Ltd., Osaka, Japan

[21] Appl. No.: 193,453

[22] Filed: Oct. 3, 1980

[30] Foreign Application Priority Data

Oct. 11, 1979 [GB] United Kingdom ................ 7935401
Oct. 15, 1979 [GB] United Kingdom ................ 7935730
Oct. 17, 1979 [GB] United Kingdom ................ 7936000
Mar. 28, 1980 [GB] United Kingdom ................ 8010459

[51] Int. Cl.³ .......................................... C07C 103/52
[52] U.S. Cl. .......................................... 260/112.5 R
[58] Field of Search ................ 424/177; 260/112.5 R; 424/85

[56] References Cited

FOREIGN PATENT DOCUMENTS 11283 5/1980 European Pat. Off.
2033906 5/1980 United Kingdom.
2053231 2/1981 United Kingdom.

OTHER PUBLICATIONS

Elloys, F. et al., Biochem. and Biophys. Res. Comm., vol. 59, pp. 1317-1325, 1974.
Kotani, S., et al., Abstracts of Societe de Chime Bioligique International Symposium, Oct. 14-15, 1974, Paris.
Dezelee, P., et al., Biochemistry, vol. 9, pp. 823-831, 1970.
Werner, et al., Immunopotentiating Activities of a Microbial Tetrapeptide After Coupling with Lauric Acid, Eleventh Int: Conference of Antimicrobial Agents & Chemotherapy, Oct. 1-5, (1979).
Chemical Abstracts, vol. 72, No. 19, May 11, 1970, p. 72, Abstract 97462z.
Biochemistry 1970, 9(4), pp. 823-831.

*Primary Examiner*—Blondel Hazel
*Attorney, Agent, or Firm*—Olbon, Fisher, Spivak, McClelland & Maier

[57] ABSTRACT

The invention relates to novel peptides and their pharmaceutically acceptable salts, particularly useful for pharmaceutical purposes such as in the therapeutic treatment of infectious diseases caused by pathogenic microorganisms. The compounds have the structure

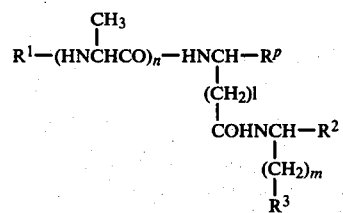

wherein
$R^1$ is hydrogen or acyl;
$R^2$ is carboxy or protected carboxy or a group of the formula: $-COHN-R_a^2$ wherein $R_a^2$ is carboxy (lower) alkyl or protected carboxy (lower) alkyl;
$R^3$ is carboxy, protected carboxy, lower alkyl, hydroxyphenyl, carbamoyl or a group of the formula:

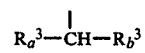

wherein $R_a^3$ is hydrogen, amino, protected amino or acylamino, $R_b^3$ is carboxy or protected carboxy;
$R^p$ is carboxy, protected carboxy, carbamoyl, carboxy (lower) alkyl or protected carboxy (lower) alkyl;
l is an integer 2,
m is an integer 0 to 2 and
n is an integer 1,
provided that,
when
$R^1$ is hydrogen or acyl,
$R^2$ is carboxy, protected carboxy or a group of the formula: $-CONHR_a^2$ wherein $R_a^2$ is carboxy (lower) alkyl or protected carboxy (lower) alkyl,
$R^p$ is carboxy, or protected carboxy, m is an integer 2, then
$R^3$ is carbamoyl, lower alkyl or hydroxyphenyl or a group of the formula:

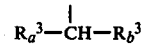

wherein $R_a^3$ is hydrogen or acylamino and $R_b^3$ is carboxy or protected caboxy, and
when
$R^p$ is carbamoyl, then
$R^1$ is acyl.

9 Claims, No Drawings

PEPTIDES, PROCESS FOR PREPARATION THEREOF AND USE THEREOF

This invention relates to a new peptide. More particularly, this invention relates to a new peptide and the pharmaceutically acceptable salt thereof, which have pharmacological activities, to processes for the preparation thereof and to a new intermediate for preparing the active peptide, and to the pharmaceutical composition comprising the same and a method of use thereof.

A new peptide of this invention is represented by the following formula (I):

$$R^1-(HNCHCO)_n-HNCH-R^p \atop \underset{\underset{R^3}{(CH_2)_m}}{\underset{COHNCH-R^2}{(CH_2)_l}} \quad\text{with}\ CH_3\ \text{on first CH} \tag{I}$$

wherein
$R^1$ is hydrogen or acyl;
$R^2$ is carboxy or protected carboxy or a group of the formula: $-COHN-R_a^2$ wherein $R_a^2$ is carboxy(lower)alkyl or protected carboxy(lower)alkyl;
$R^3$ is a carboxy, protected carboxy, lower alkyl, hydroxyphenyl, carbamoyl or a group of the formula:

$$R_a^3-\underset{|}{CH}-R_b^3$$

wherein $R_a^3$ is hydrogen, amino, protected amino or acylamino, $R_b^3$ is carboxy or protected carboxy;
$R^p$ is carboxy, protected carboxy, carbamoyl, carboxy(lower)alkyl or protected carboxy(lower)alkyl;
l is an integer 0 or 2,
m is an integer 0 to 3 and
n is an integer 0 to 1, provided that,
when
$R^1$ is hydrogen or acyl excepting N-acetylmuramyl,
$R^2$ is carboxy, protected carboxy or a group of the formula: $-CONH-R_a^2$ wherein $R_a^2$ is carboxy(lower)alkyl or protected carboxy(lower)alkyl,
$R^3$ is a group of the formula:

$$R_a^3-\underset{|}{CH}-R_b^3$$

wherein $R_a^3$ is amino or protected amino, $R_b^3$ is carboxy or protected carboxy, l is an integer 2, m is an integer 3 and n is an integer 0 to 1, then
$R^p$ is carbamoyl, carboxy(lower)alkyl or protected carboxy(lower)alkyl, and
when
$R^1$ is hydrogen or acyl,
$R^2$ is carboxy, protected carboxy or a group of the formula: $-CONHR_a^2$ wherein $R_a^2$ is carboxy(lower)alkyl or protected carboxy(lower)alkyl,
$R^p$ is carboxy, or protected carboxy, l is an integer 2, m is an integer 3 and n is an integer 0 to 1, then $R^3$ is carbamoyl, lower alkyl or hydroxyphenyl or a group of the formula:

$$R_a^3-\underset{|}{CH}-R_b^3$$

wherein $R_a^3$ is hydrogen or acylamino and $R_b^3$ is carboxy or protected carboxy and
when $R^p$ is carbamoyl and n is an integer 1, then $R^1$ is acyl.

Particulars of the various definitions, which are mentioned hereinabove, and hereinafter and preferred examples thereof are explained in the following.

The term "lower" is intended to mean a group having 1 to 6 carbon atom(s), unless otherwise provided.

(1) Re. Acyl for $R^1$, $R_a^1$ and $R_e^3$, and acyl moiety of acylamino for $R_a^3$ and $R_d^3$ Generally, "acyl" may be an acyl group derived from an acid such as organic carboxylic acid or carbonic acid, each of which more particularly includes an aliphatic, an aromatic and/or a heterocyclic groups in its molecule.

Suitable examples of said acyl are illustrated below.

Aliphatic acyl means an acyl group derived from an aliphatic acid and includes:

alkanoyl (e.g. formyl, acetyl, propionyl, butyryl, isobutyryl, valeryl, isovaleryl, pivaloyl, hexanoyl, α-ethyl-hexanoyl, heptanoyl, lauroyl, stearoyl, docosanoyl, a group of the formula: $CH_3(CH_2)_{31}CO$, $[CH_3(CH_2)_{21}]_2CHCO$, $[CH_3(CH_2)_{15}]_2CHCO$, $CH_3(CH_2)_{41}CO$, etc.); lower alkoxycarbonyl (e.g. methoxycarbonyl, ethoxycarbonyl, propoxycarbonyl, butoxycarbonyl, t-butoxycarbonyl, t-pentoxycarbonyl, etc.) and the like.

In the above exemplified aliphatic acyl, the alkane moiety may have optionally one or more suitable substituent(s) such as amino, halogen (e.g. fluorine, chlorine, bromine, etc.), hydroxy, hydroxyimino, carboxy, lower alkoxy (e.g. methoxy, ethoxy, propoxy, etc.), lower alkoxycarbonyl, acylamino such as lower alkanoylamino (e.g. formamido, acetamido, propionamido, etc.).

Preferred examples of alkanoyl having such substituents may be exemplified by $$\text{lactoyl (i.e. } CH_3\overset{OH}{\underset{|}{C}}HCO-\text{ )},$$

$$\text{alanyl (i.e. } H_2N\overset{CH_3}{\underset{|}{C}}HCO-\text{ )},$$

$$\text{glutamyl (i.e. } H_2N\overset{CO-}{\underset{|}{C}}\underset{(CH_2)_2}{HCOOH}\text{ )},$$

lactoyl-alanyl-γ-glutamyl-diaminopimelyl-alanyl
(i.e. $CH_3\overset{OH}{\underset{|}{C}}HCONH\overset{CH_3}{\underset{|}{C}}HCONHCHCOOH$
$\underset{\underset{\underset{H_2NCHCOOH}{(CH_2)_3}}{COHNCHCOHNCHCO-}}{(CH_2)_2}\overset{CH_3}{\underset{|}{}}$ ), lactoyl-alanyl-γ-glutamyl-diaminopimelyl-glycyl -continued

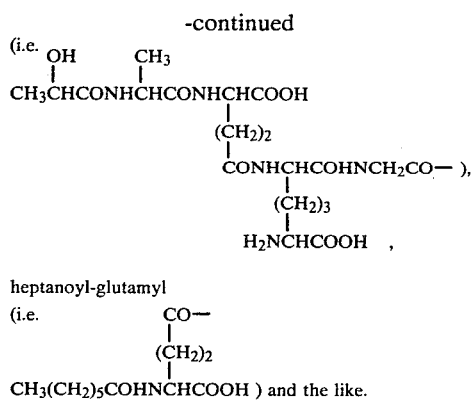

heptanoyl-glutamyl (i.e.
CH₃(CH₂)₅COHNCHCOOH
           |
          (CH₂)₂
           |
           CO—    ) and the like.

Aromatic acyl means an acyl group derived from an acid having substituted or unsubstituted aryl group, in which the aryl group may include phenyl, tolyl, xylyl, naphthyl and the like, and suitable examples thereof are illustrated as follows:

aroyl (e.g. benzoyl, toluoyl, xyloyl, naphthoyl, phthaloyl, etc.);

aralkoxycarbonyl (e.g. benzyloxycarbonyl, benzhydryloxycarbonyl, trityloxycarbonyl, α-naphthylmethoxycarbonyl, etc.) and the like.

In the above exemplified aromatic acyl, the aromatic hydrocarbon moiety (particularly aryl moiety) and/or aliphatic hydrocarbon moiety (particularly alkane moiety) may have optionally one or more suitable substituent(s), such as the same as those exemplified as the suitable substituent for alkane moiety as mentioned above.

Hetorocyclic acyl means an acyl group derived from an acid having heterocyclic group and includes:

heterocyclic carbonyl, in which the heterocycle moiety is 5 to 6 membered heterocycle containing at least one hetero atom selected from nitrogen, oxygen and sulfur (e.g. thenoyl, furoyl, pyrrolecarbonyl, 5-oxo-2-pyrrolidinecarbonyl, nicotinoyl, etc.) and the like.

In the above exemplified heterocyclic acyl, heterocycle moiety and/or the aliphatic hydrocarbon moiety may have optionally one or more suitable substituent(s) such as the same as those exemplified as the suitable substituent for aliphatic acyl as mentioned above.

Further, in the above exemplified acyl, in case that these acyls have one or more functional group such as hydroxy, amino, carboxy and the like, such groups may be protected by conventional protective group(s).

(2) Re. Protected carboxy or protected carboxy moiety for $R^2$, $R_a^2$, $R^p$, $R_1^p$, $R^3$, $R_c^3$, $R_b^2$, $R_b^3$ and $R_f^3$:

A protective group of the protected carboxy includes a conventional protective group for tentatively protecting a carboxy group which is conventionally used in the field of amino acid and peptide chemistry.

As preferred examples of the protected carboxy, there may be exemplified an ester such as an ester with silyl compound (hereinafter referred to as silyl ester), an ester with an aliphatic hydroxy compound (hereinafter referred to as apliphatic ester) and an ester with a hydroxy compound containing an aromatic group (hereinafter referred to as aromatic ester), and a protected carbazoyl of the formula: —COHNNHY (wherein Y is hydrogen or an amino protective group).

Concrete examples of such a protected carboxy are exemplified as follows:

suitable silyl ester such as trialkylsilyl (e.g. trimethylsilyl, triethylsilyl, etc.) ester, halo-alkylsilyl (e.g. chloro-dimethylsilyl, dichloromethylsilyl, etc.) ester, trihalosilyl (e.g. trichlorosilyl, etc.) ester, alkylalkoxysilyl (e.g. methyl-diethoxysilyl, etc.) ester, trialkoxysilyl (e.g. tris(2-chloroethoxy)silyl, etc.) ester, and the like;

suitable aliphatic hydrocarbon ester such as alkyl (e.g. methyl, ethyl, propyl, isopropyl, butyl, tertbutyl, etc.) ester, cycloalkyl (e.g. cyclopentyl, cyclohexyl, etc.) ester and the like; and suitable ester containing an aromatic group such as aryl (e.g. phenyl, tolyl, xylyl, etc.) ester, aralkyl (e.g. benzyl, diphenylmethyl, phenethyl, etc.) ester, aryloxyalkyl (e.g. phenoxymethyl, phenoxyethyl, etc.) ester, aroylaklyl (e.g. phenacyl, toluoylethyl, etc.) ester, and the like.

The ester forming group (e.g. substituted silyl, aliphatic hydrocarbon residue, aryl, aralkyl, aryloxyalkyl, aroylalkyl and the like, as exemplified above) may optionally have one or more appropriate substituent(s) such as alkyl, (e.g. methyl, ethyl, etc.), cycloalkyl (e.g. cyclopropyl, cyclohexyl, etc.), alkoxy (e.g. methoxy, ethoxy, etc.), alkanoyloxy (e.g. acetoxy, etc.), alkylthio (e.g. methylthio, etc.), halogen (e.g. chlorine, etc.), cyano, nitro, etc.

Examples of such substituted esters may be mono(di or tri)haloalkyl (e.g. chloromethyl, bromoethyl, dichloromethyl, 2,2,2-trichloroethyl, 2,2,2-tribromoethyl, 2,2,2-trifluoroethyl, etc.) ester, cyanoalkyl (e.g. cyanomethyl, cyanoethyl, etc.) ester, cycloalkyl-substituted-alkyl (e.g. 1-cyclopropylethyl, etc.) ester, mono(di, tri, tetra or penta)halophenyl (e.g. 4-chlorophenyl, 3,5-dibromophenyl, 2,4,5-trichlorophenyl, 2,4,6-trichlorophenyl, pentachlorophenyl, etc.) ester, and the like.

(3) Re. A group of the formula:

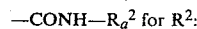

—CONH—$R_a^2$ for $R^2$:

Suitable example of lower alkyl moiety of carboxy(lower)alkyl and protected carboxy(lower)alkyl for $R_a^2$ is one having 1–6 carbon atoms such as methyl, ethyl, propyl, isopropyl, butyl, isobutyl, pentyl, isopentyl, hexyl and the like.

Suitable example of such a protected carboxy in the protected carboxy(lower)alkyl is the same as that exemplified for $R^p$, $R^3$, $R^2$ and $R_b^3$.

Most preferred examples of a group of the formula: —CONH—$R_a^2$ are illustrated as follows:

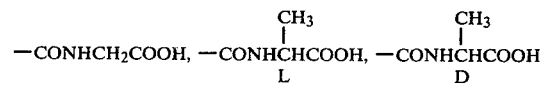

and the corresponding group, in which the carboxy group is protected by a conventional carboxy protective group as mentioned hereinabove.

(4) Re. Amino protective group of protected amino for $R_a^3$, Y, $R_d^3$ and $R_h^3$:

The amino protective group includes a conventional protective group for tentatively protecting an amino group, which is used in the field of amino acid and peptide chemistry. That is, in the peptide synthesis, it is understood that, for bonding a desired "reactive" amino group (—NH₂) with a desired "reactive" carboxy group (—COOH) to form a desired peptide bond (—CONH—) between them, it is preferable to tentatively protect the other undesired "reactive" amino group to convert it into an unreactive or less reactive protected amino group in the reaction in order to avoid the side reaction between the undesired "reactive" amino group and desired "reactive" carboxy groups. Further, it is understood that it is preferable that a protective group in such protected amino group is easily eliminable according to the necessity in the post treatment of the object peptide. Accordingly, an amino protective group to meet the above requirements can be used and suitable one should be selected according to the kind and property of the component to be used in this invention.

As preferred examples of the amino protective group, the following examples are illustrated:

Acyl, particularly organic acyl, for example, substituted or unsubstituted aliphatic hydrocarbonoxycarbonyl type acyl and such as alkoxycarbonyl (e.g. methoxycarbonyl, ethoxycarbonyl, propoxycarbonyl, butoxycarbonyl, t-butoxycarbonyl, t-pentoxycarbonyl, etc.), haloalkoxycarbonyl (e.g. chloromethoxycarbonyl, tribromoethoxycarbonyl, trichloroethoxycarbonyl, etc.), alkane- or arene-sulfonylalkoxycarbonyl (e.g. 2-(mesyl)ethoxycarbonyl, 2-(p-toluenesulfonyl)ethoxycarbonyl, etc.), alkylthio- or arylthioalkoxycarbonyl (e.g. 2-(ethylthio)ethoxycarbonyl, 2-(p-tolylthio)ethoxycarbonyl, etc.), monocyclic or fusedcyclic-alicyclic oxycarbonyl (e.g. cyclohexyloxycarbonyl, adamantyloxycarbonyl, isobornyloxycarbonyl, etc.), substituted or unsubstituted alkenyloxycarbonyl (e.g. allyoxycarbonyl, etc.), substituted or unsubstituted alkynyloxycarbonyl (e.g. 1,1-dimethylpropargyloxycarbonyl, etc.) or the like;

substituted or unsubstituted aryloxycarbonyl (e.g. phenoxycarbonyl, p-methylphenoxycarbonyl, etc.), substituted or unsubstituted aralkoxycarbonyl (e.g. benzyloxycarbonyl, p-nitrobenzyloxycarbonyl, p-phenylazobenzyloxycarbonyl, p-(p-methoxyphenylazo)benzyloxycarbonyl, p-chlorobenzyloxycarbonyl, p-bromobenzyloxycarbonyl, α-naphthylmethoxycarbonyl, p-biphenylisopropoxycarbonyl, etc.);

sulfonyl type acyl such as substituted or unsubstituted arenesulfonyl (e.g. benzenesulfonyl, p-toluenesulfonyl, etc.);

phosphonyl type acyl such as substituted or unsubstituted dialkylphosphoryl (e.g. dimethylphosphoryl, etc.);

substituted or unsubstituted diaralkylphosphoryl (e.g. O,O-dibenzylphosphoryl, etc.) and the like;

substituted or unsubstituted alkanoyl such as halo(lower)alkanoyl (e.g. formyl, trifluoroacetyl, etc.), substituted or unsubstituted aryloxyalkanoyl (e.g. phenoxyacetyl, p-chlorophenoxyacetyl, 2-nitrophenoxyacetyl, 2-methyl-2-(2-nitrophenoxy)propyonyl, etc.) or the like;

aralkyl, particularly, mono, di or tri substituted or unsubstituted phenylmethyl such as benzyl, diphenylmethyl, trityl, nitrobenzyl, or the like;

a methanone type group such as substituted or unsubstituted alkylidene (e.g. ethylidene, isopropylidene, etc.) or the like;

substituted or unsubstituted aralkylidene such as benzylidene, 2-hydroxybenzylidene, 2-hydroxy-5-chlorobenzylidene or the like;

a sulfenyl such as substituted or unsubstituted arylthio such as phenylthio, nitrophenylthio, dinitrophenylthio, trichlorophenylthio or the like; and substituted or unsubstituted aralkylthio such as tritylthio or the like.

(5) Re. Lower alkyl for $R^3$ and lower alkyl moiety for $R^p$

Suitable example of such lower alkyl is one having 1 to 6 carbon atoms such as methyl, ethyl, propyl, isopropyl, butyl, isobutyl, pentyl, isopentyl and the like.

A pharmaceutically acceptable salt of the new peptides of the formula (I) may include a salt with an inorganic or organic base such as an alkali metal salt (e.g. sodium salt, potassium salt, etc.), an alkaline earth metal salt (e.g. calcium salt, etc.), ammonium salt, ethanolamine salt, triethylamine salt, dicyclohexylamine salt or the like, and an acid addition salt with organic or inorganic acid such as methane sulfonate, hydrochloride, sulfate, nitrate, phosphate or the like.

The compound (I) of this invention can be prepared by various methods, details of which will be apparent from the following descriptions.

(1) Process 1: peptide bond formation 1

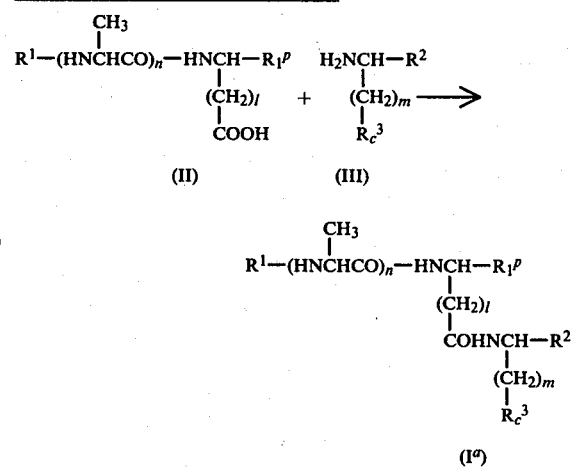

(2) Process 2: Peptide bond formation 2

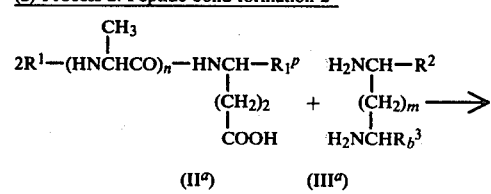

-continued
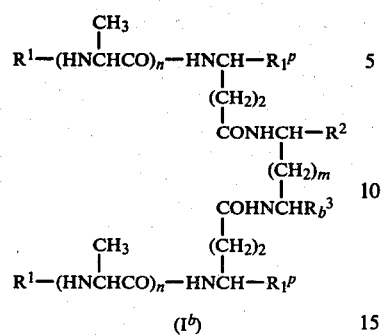
(I$^b$)
(3) Process 3: Selection deacylation
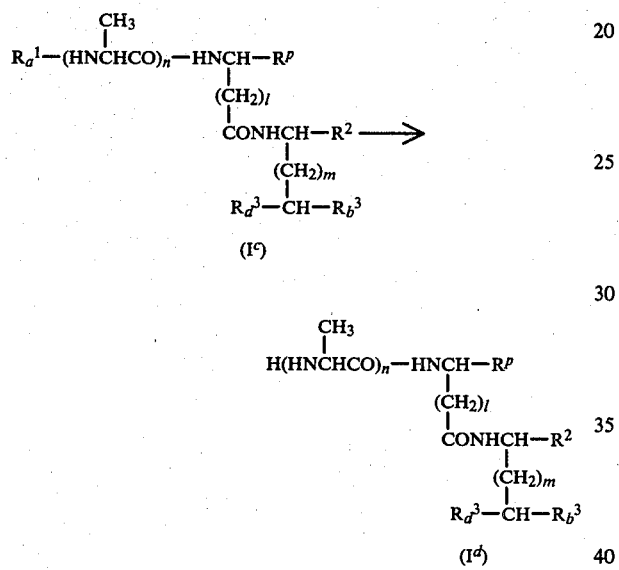
(4) Process 4: Acylation 1
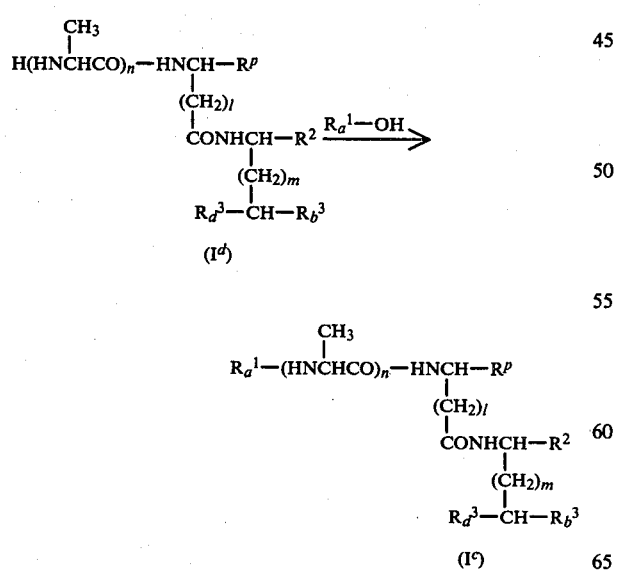
(5) Process 5: Elimination of amino protective group
-continued
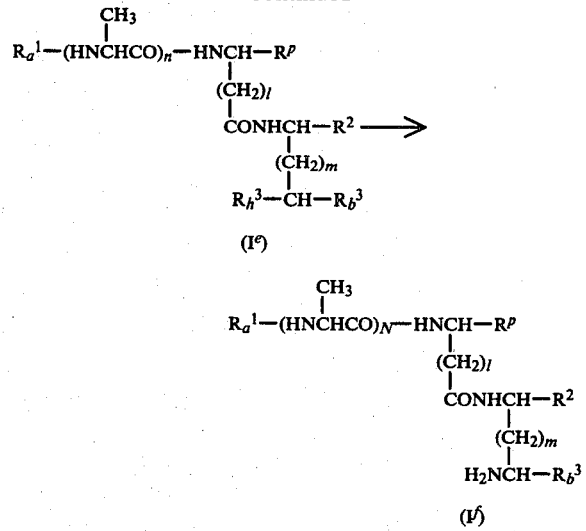
(I$^f$)
(6) Process 6: Acylation 2
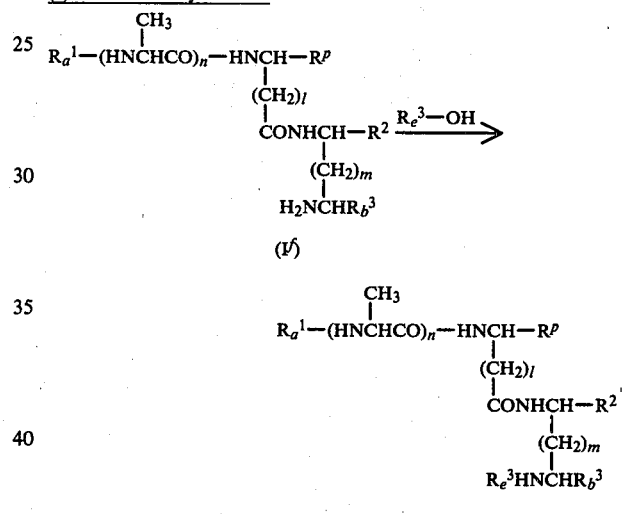
(I$^g$)
(7) Process 7: Elimination of protective groups
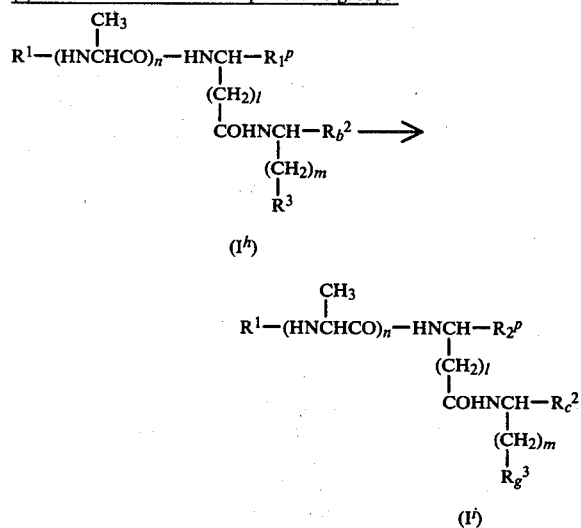
(I$^i$)
Wherein R$_1{}^p$ is protected carboxy, protected carboxy(lower)alkyl or carbamoyl, R$_c{}^3$ is carboxy, protected carboxy, lower alkyl, hydroxyphenyl, carbamoyl or a group of the formula:

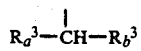

wherein $R_a^3$ is hydrogen, protected amino or acylamino, $R_b^3$ is carboxy or protected carboxy, $R_a^1$ is acyl, $R_d^3$ is hydrogen, protected amino or acylamino, $R_h^3$ is protected amino, $R_e^3$ is acyl, $R_2^p$ is carboxy, carbamoyl or carboxy(lower)alkyl, $R_b^2$ is protected carboxy or a group of the formula: —COHNR$_a^2$ wherein $R_a^2$ is protected carboxy(lower)alkyl, $R_c^2$ is carboxy or a group of the formula: —COHNR$_a^2$ wherein $R_a^2$ is carboxy(lower)alkyl, $R_g^3$ is carboxy, lower alkyl, hydroxyphenyl, carbamoyl or a group of the formula:

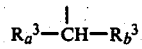

wherein $R_a^3$ is amino or acylamino, $R_b^3$ is carboxy, and $R^1$, $R^2$, $R^3$, $R^p$, l, m and n are each as defined above.

Detailed explanation of processes for preparing of a compound (I) will be made in the following.

(1) Process 1: Peptide bond formation 1

Compound (II)+Compound (III)→Compound (Ia)

This process relates to a method for preparing Compound (Ia) by reacting Compound (II) or its salt with a Compound (III) or its salt.

The reaction of this process can be conducted as follows.

That is, in one case, as the first step, the carboxy group of Compound (II) or its salt is usually activated in a conventional manner, for example, in the form of its acid halide, azide, acid anhydride or a mixed anhydride, activated ester, and the like, and is reacted with the Compound (III) to give Compound (Ia), and in the other case, the Compound (II) or its salt is reacted with the Compound (III) or its salt directly in the presence of a conventional condensing agent such as N,N-dicyclohexylcarbodiimide and the like. Among these activation methods, preferred activation method for the carboxy group of the Compound (II) into its activated form and preferred condensing agent as mentioned above are selected according to kinds of the carboxy protective group(s) of the Compound (II) and (III) and to the reaction conditions (e.g. the kinds of the reaction solvent, reaction temperature and so on).

This reaction is preferably carried out in a solvent such as methylene chloride, chloroform, tetrahydrofuran, dioxane, ethyl acetate, methanol, ethanol, water or the like under ice-cooling to at ambient temperature and the reaction in the presence of a condensing agent is usually carried out in an anhydrous, but not critical, conditions.

(2) Process 2: Peptide bond formation 2

Compound (II$^a$)+Compound (III$^a$)→Compound (I$^b$)

This process relates to a method for preparing Compound (I$^b$) by reacting Compound (II$^a$) or its salt with a Compound (III$^a$) or its salt.

This reaction is carried out in substantially the same manner as that of Process 1.

(3) Process 3: Selective deacylation

Compound (I$^c$)→Compound (I$^d$)

This process relates to a method for preparing Compound (I$^d$) or its salt by removing selectively an acyl group for $R_a^1$ of Compound (I$^c$) or its salt.

This process is applied to case that the acyl group for $R_a^1$ reveals a different chemical property from that of the amino protective group of protected amino or acyl of acylamino for $R_d^3$ against each kind of the removal methods and can selectively be removable by a method to be employed.

This reaction is carried out by conventional methods such as catalytic reduction method, liquidammoniaalkalimetal method, acid method, zinc acid method, base method, hydrazine method and the like. Among these methods, preferred one is selected according to kind of the acyl group for $R_a^1$ of Compound (I$^c$).

Each of the above methods is explained as follows.

(i) Catalytic reduction method:

This method is preferably applied to case that the acyl group for $R_a^1$ of Compound (I$^c$) are one which is removable by catalytic reduction. As preferred examples of such an acyl group for $R_a^1$, there may be exemplified substituted or unsubstituted aralkoxycarbonyl (e.g. benzyloxycarbonyl, etc.) and the like.

This catalytic reduction is carried out in a conventional manner, and suitable catalysts to be used in catalytic reduction are conventional ones such as platinum catalyst (e.g. platinum plate, spongy platinum, platinum black, colloidal platinum, platinum oxide or platinum wire, etc.), palladium catalyst (e.g. spongy on carbon, colloidal palladium, palladium on barium sulfate, palladium on barium carbonate, etc.), nickel catalyst (e.g. reduced nickel, nickel oxide, Raney nickel, etc.), cobalt catalyst (e.g. reduced cobalt, Raney cobalt, etc.), iron catalyst (e.g. reduced iron, Raney iron, etc.), copper catalyst (e.g. reduced copper, Raney copper, Ullman copper, etc.) or the like.

The reduction is usually carried out in a solvent. A suitable solvent to be used may be, e.g. water, methanol, ethanol, propanol, ethyl acetate, tetrahydrofuran, dioxane, N,N-dimethylformamide, acetic acid, a mixture of water and alcohol (e.g. methanol, ethanol, etc.) tetrahydrofuran, dioxane or ethyl acetate, and other conventional organic solvent or a mixture thereof. Further, the reduction is preferably carried out in the presence of an acid such as acetic acid or the like.

The reaction is preferably carried out under somewhat milder conditions such as cooling or warming.

(ii) Acid method:

(ii)-1 Method of use of trifluoroacetic acid or formic acid:

This method is preferably applied to case that the acyl group for $R_a^1$ is one which is removable by treating with trifluoro-acetic acid or formic acid. Preferred examples of such an acyl group may be exemplified by a group such as branched- or alicyclicoxycarbonyl, (e.g. t-butoxycarbonyl, t-pentoxycarbonyl) and the like.

This reaction is conventionally carried out in a solvent such as methylene chloride, chloroform, acetic acid, water and the like in the presence of trifluoroacetic acid or formic acid, and anisole is preferably added thereto.

Trifluoroacetic acid and formic acid are also used as the solvent.

This reaction is usually carried out under ice-cooling to at ambient temperature.

(ii)-2 Method of use of hydrochloric acid or p-toluenesulfonic acid:

This method is preferably applied to case that an acyl group for $R_a^1$ is one which is removed by treating with hydrochloric acid or p-toluenesulfonic acid.

Preferred examples of such an acyl group may be exemplified by e.g. substituted or unsubstituted branched alkoxycarbonyl (e.g. t-butoxycarbonyl, 1-(p-biphenyl)-1-methylethoxycarbonyl, etc.) and the like in addition to one as illustrated in the above (ii)-1.

This reaction is carried out in a solvent such as ethyl acetate, methylene chloride, chloroform, tetrahydrofuran and the like in the presence of an inorganic or organic strong acid such as hydrochloric acid, p-toluenesulfonic acid or the like, and anisole is preferably added thereto.

This reaction is preferably carried out under ice-cooling to at ambient temperature.

(ii)-3 Method of use of hydrogen bromide:

This method is preferably applied to case that an acyl group for $R_a^1$ is one which is removable by treating with hydrogen bromide.

Preferred examples of such an acyl group may be exemplified by substituted or unsubstituted aralkoxycarbonyl (e.g. benzyloxycarbonyl, etc.) and an alkoxycarbonyl (e.g. isopropoxycarbonyl, etc.) in addition to one as illustrated in the above (ii)-1 and (ii)-2.

This reaction is usually carried out in a solvent such as ethyl acetate, acetic acid, trifluoroacetic acid or the like in the presence of hydrogen bromide.

This reaction is preferably carried out under ice-cooling to at ambient temperature.

(iii) Liquid-ammonia-alkali metal method:

This method is preferably applied to case that the acyl group for $R_a^1$ is one which is removable by treating with liquid ammonia-alkali metal. As preferred examples of such an acyl group, there may be exemplified substituted or unsubstituted aralkoxycarbonyl (e.g. benzyloxycarbonyl, etc.) and the like.

This reaction is usually carried out by dissolving Compound ($I^c$) into liquid ammonia and then alkali metal is added thereto.

This reaction is preferably carried out at a lower temperature, e.g. at $-78°$ C. to at boiling point of liquid ammonia.

(iv) Hydrazine method:

This method is preferably applied to case that the acyl group for $R_a^1$ is one which is removable by treating with a hydrazine compound or an amine compound.

Preferred examples of hydrazine compound are exemplified by hydrazine, methylhydrazine, phenylhydrazine and the like and those of amine compound are exemplified by hydroxylamine, dialkylaminoalkylamine (e.g. N,N-dimethylaminopropylamine, etc.) and the like.

This reaction is usually carried out by treating Compound ($I^c$) with the hydrazine compound or amine compound in a solvent such as water, alcohol (e.g. methanol, ethanol, etc.) tetrahydrofuran, dioxane or the like at ambient temperature to under reflux.

(v) Zinc-acid method:

This method is preferably applied to case that the acyl group for $R_a^1$ is one which is removable by treating with zinc acid.

This method is carried out by treating Compound ($I^c$) with zinc in the presence of a weak acid such as formic acid, acetic acid and the like. The reaction may be carried out in a solvent such as methylene chloride, chloroform, tetrahydrofuran, ethyl acetate, alcohol (e.g. methanol, ethanol, etc.), dimethylformamide and the like, and in this case a weak acid as mentioned above is added to such a solvent. The reaction is usually carried out at $-10°$ C. to ambient temperature.

(vi) Base method:

This method is preferably applied to case that the acyl group for $R_a^1$ is one which is removable by treating with a base.

This method is carried out in the presence of a base under ice-cooling to at ambient temperature.

Suitable base is an inorganic base such as alkali metal hydroxide or alkaline earth metal hydroxide, or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butylamine, N,N-dimethyl-1, 3-propanediamine, trimethylamine, triethylamine, etc.), unsubstituted, mono- or disubstituted arylamine (e.g. aniline, N-methylaniline, N,N-dimethylaniline, etc.), a heterocyclic base (e.g. pyrrolidine, morpholine, N-methylmorpholine, N-methylpiperidine, N,N-dimethylpiperazine, pyridine, etc.) or the like; a basic ion exchange resin and the like.

This method is preferably conducted under somewhat milder conditions such as cooling or warming and usually in any solvent which does not have an adverse influence on the reaction, e.g. water, a hydrophilic solvent such as alcohol (e.g. methanol, ethanol, propanol, etc.), N,N-dimethylformamide, tetrahydrofuran, dioxane, dimethylsulfoxide, etc. or a mixture thereof. In case that the above-mentioned bases are in liquid, they can also be used as a solvent.

In this process, in case that the acyl group for $R_d^3$ has protective group(s), such protective group(s) may simultaneously be removed, and in case that the carboxy protective group of the protected carboxy or the protected carboxy(lower)alkyl for RP is, for example, substituted or unsubstituted aralkyl type (e.g. benzyl), such protective group may simultaneously removed, and such cases are include in this process.

(4) Process 4:

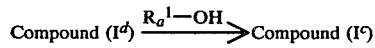

Compound ($I^d$) $\xrightarrow{R_a^1-OH}$ Compound ($I^c$)

This process relates to a method for preparing Compound ($I^c$) by reacting Compound ($I^d$) with an acylating agent.

The acylating agent to be used in this reaction includes an organic acid ($R_a^1$—OH wherein $R_a^1$ is acyl group) such as monobasic or dibasic organic carboxylic acid or an organic carbonic acid, and more particularly, aliphatic, aromatic or heterocyclic carboxylic acid, and the corresponding carbonic; their reactive derivatives. Suitable examples of these organic acid ($R_a^1$—OH wherein $R_a^1$ is acyl group) are the corresponding organic acid to those comprising the acyl group as exemplified hereinabove in details in the descriptions of suitable examples of acyl groups for $R^1$ and $R_a{}^1$ of the compound (I).

Said organic acid as an acylating agent can be used in the form of an activated organic acid, i.e. as a reactive derivative of the acid. As such reactive derivatives of said organic acids, there may be exemplified an acid halide, an acid azide, an acid anhydride, an activated amide, an activated ester, etc. Preferred examples of such reactive derivatives are illustrated by:

an acid halide (e.g. acid chloride, acid bromide etc.);
an acid azide;
an acid anhydride including a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, monoalkylcarbonic acid, aliphatic carboxylic acid (e.g. acetic acid, pivalic acid, pentanoic acid, isopentanoic acid, 2-ethylbutyric acid, trichloroacetic acid, etc.), aromatic carboxylic acid (e.g. benzoic acid, etc.) or the like; and symmetrical acid anhydride;
an activated amide with pyrazole, imidazole, 4-substituted imidazole, dimethylpyrazole, triazole or tetrazole; and
an activated ester such as substituted or unsubstituted alkylthio ester (e.g. methylthio ester, carboxymethyl thioester, etc.), substituted or unsubstituted aryl thioester (e.g. phenyl thioester, p-nitrophenyl thioester, p-cresyl thioester, etc.), heterocyclic ester (e.g. pyranyl ester, pyridyl ester, piperidyl ester, 8-quinolyl thioester, etc.) or ester with N,N-dimethylhydroxylamine, 1-hydroxy-2-(H)-pyridone, N-hydroxysuccinimide, N-hydroxyphthalimide or 1-hydroxy-6-chlorobenzotriazole, or the like.

The above reactive derivative is selected according to the kind of the acid to be used.

In the reaction, when free acid is used as an acylating agent, the acylation reaction may preferably be conducted in the presence of a condensing agent such as carbodiimidic compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus compound (e.g. phosphorus oxychloride, phosphorus trichloride, etc.), thionyl chloride, oxalyl chloride, 2-ethyl-7-hydroxybenzisoxazolium salt, 2-ethyl-5-(m-sulfophenyl)isoxazolium hydroxide, (chloromethylene)dimethylammonium chloride,2,2,4,4,6,6,-hexachloro-1,3,5,2,4,6-triazatriphosphorine, 1-benzenesulphonyloxy-6-chloro-1H-benzotriazole, p-toluenesulfonyl chloride, isopropoxybenzenesulfoxyl chloride or the like; or a mixed condensing agent such as a mixture of triphenylphosphine and a carbon tetrahalide (e.g. carbon tetrachloride, carbon tetrabromide, etc.), a complex of N,N-dimethylformamide with phosphoryl chloride, phosgene or thionyl chloride, etc., or the like.

The reaction is usually conducted in a solvent such as water, alcohol (e.g. methanol, ethanol, propanol, etc.), acetone, ethyl ether, dioxane, acetonitrile, ethylacetate, N,N-dimethylformamide, dimethylsulfoxide, tetrahydrofuran, dichloromethane, chloroform, etc. or pyridine, N-methylmorpholine, N-methylpyrrolidine or other conventional solvents, or a mixture thereof. The reaction can also be conducted preferably in the presence of an organic or inorganic base such as alkali metal (e.g. sodium, potassium, etc.), alkaline earth metal (e.g. calcium, etc.), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate, lithium carbonate, etc.), alkali or alkaline earth metal alkoxide (e.g. sodium ethoxide, lithium methoxide, magnesium methoxide, etc.), trialkylamine (e.g. triethylamine, etc.), pyridine, bicyclodiaza compound (e.g. 1,5-diazabicyclo[3,4,0]nonene-5, 1,5-diazabicyclo[5,4,0]undecene-5, etc.) or the like. Among said base, a liquid one can also be used as a solvent.

There is no limitation to this reaction temperature, and this reaction may preferably be conducted within the range of cooling to ambient temperature.

In this process, in case that the acyl group for $R_d{}^3$ has a protective groups, such a protective group may be removed in the procedure of a post-treatment or by subjecting the reaction product to elimination reaction of protective group such as the aftermentioned Process 7, and such cases are included in this process.

(5) Process 5: Elimination of amino protective group

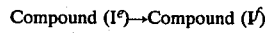
Compound ($I^e$)→Compound ($I^f$)

This process relates to a method for preparing Compound ($I^f$) by subjecting Compound ($I^e$) to elimination reaction of amino protective group of protected amino for $R_h{}^3$.

This reaction is carried out substantially in the same manner as that of Process 3.

(6) Process 6: Acylation 2

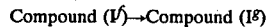
Compound ($I^f$)→Compound ($I^g$)

This process relates to a method for preparing Compound ($I^g$) by reacting Compound ($I^f$) with an acylating agent.

The acylating agent to be used in this reaction is the same as illustrated in the explanation of Process 4.

The reaction is carried out substantially in the same manner as that of Process 4.

(7) Process 7: Elimination of protective groups

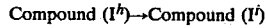
Compound ($I^h$)→Compound ($I^i$)

This process relates to a method for preparing Compound ($I^i$) by subjecting Compound ($I^h$) to removal reaction of protective groups of protected carboxy groups for $R_1{}^p$, $R_b{}^2$ and $R_b{}^3$ and or amino protective group of protected amino for $R_a{}^3$, details of which are explained as follows:

Process 7-1: Elimination of an amino protective group of protected amino

The elimination of an amino protective group is carried out substantially in the same manner as that of Process 3, and accordingly the detailed explanation for Process 3 as made hereinabove is to be referred to.

In this method, in case that an acyl for $R^1$ is the same as the amino protective group of the protected amino for $R_a{}^3$, then such acyl group is simultaneously removed.

Process 7-2: Removal of carboxy protective group of protected carboxy

The reaction for removal of protective group of the protected carboxy group is carried out by a conventional method such as hydrolysis and reduction or the like, details of which are explained in the following.

(i) For hydrolysis which refers to the same meaning as solvolysis including, for example, acidolysis, alcoholysis, aminolysis, hydroxinolysis, etc.:

Hydrolysis is preferably carried out in the presence of an acid or base.

Suitable acid includes an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion-exchange resin and the like.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butylamine, N,N-dimethyl-1,3-propanediamine, trimethylamine, triethylamine, etc.), unsubstituted, mono- or disubstituted arylamine (e.g. aniline, N-methylaniline, N,N-dimethylaniline, etc.), a heterocyclic base (e.g. pyrrolidine, morpholine, N-methylmorpholine, N-methylpiperidine, N,N-dimethylpiperazine, pyridine, etc.), hydrazines (e.g. hydrazine, methyhydrazine, ethylhydrazine, etc.) or the like; a basic ion-exchange resin and the like.

The hydrolysis is preferably conducted under somewhat milder conditions such as cooling or warming and usually in a solvent which does not have adverse influence to the reaction, e.g. water, a hydrophilic solvent such as alcohol (e.g. methanol, ethanol, propanol, etc.), acetone, N,N-dimethylformamide, tetrahydrofuran, dioxane, dimethylsulfoxide, etc. or a mixture thereof, and other hydrophobic solvent such as benzene diethylether, etc. may also be used as a solvent. A liquid abovementioned acid or base can also be used as solvent.

(ii) For reduction:

Reduction, including chemical reduction and catalytic reduction, is carried out in a conventional manner.

Suitable reducing agents to be used in chemical reduction are a metal (e.g. tin, zinc, iron, etc.), or a combination of such metal and/or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum platinum black, colloidal platinum, platinum oxide or platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Rabey nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) or the like.

The reduction is usually carried out in a solvent. A suitable solvent to be used may be, e.g. water, alcohol (e.g. methanol, ethanol, propanol, etc.) and other conventional organic solvent or a mixture thereof. Additionally, the afore-mentioned liquid acids to be used in chemical reduction can also be used as solvent. Further, a suitable solvent to be used in catalytic reduction may be, e.g. the above-mentioned solvent, and other conventional solvent, such as diethyl ether, dioxane, tetrahydrofuran, etc. or a mixture thereof.

The reaction is preferably carried out under somewhat milder conditions such as cooling or warming.

Among these methods for removal of protective groups, preferred one and appropriate combination methods are to be selected according to kinds of the protective groups of carboxy group and amino protective group to be removed off.

It is noted that this process includes the following cases of removal of protective groups, that is, one case that all of the carboxy protective groups for $R_1^p$, $R_b^2$ and $R_b^3$ and the amino protective group for $R_a^3$ in the Compound (I$^t$) are simultaneously removed by a method to be employed to the reaction, and the other case that the carboxy protective groups and the amino protective group are sequentially and stepwise removed by a method which is appropriately selected according to the kinds of the protective group to be removed.

Process 7-3: Removal of hydrazino group

A protected carbazoyl of the formula: —CONHNHY wherein Y is an amino protective group can be removed by subjecting the Compound (I$^t$) at first to the reaction of Process 7-1 for eliminating amino protective group (i.e. Y) to give —CO.NHNH$_2$ group and then subjecting the reaction product to the reaction of this step to give —COOH group, and particular of this reaction step is as follows.

The reaction of this step is carried out in a conventional manner by treating the Compound (I$^t$) with a conventional oxidizing agent which is capable of oxidizing a group of the formula: —CONHNH$_2$ to form into a group of the formula: —COOH and accordingly preferred example of such an oxidizing agents may be halogen such as iodine, bromine etc., perhalogenic acid such as periodic acid or its salt (e.g. sodium salt, potassium salt, etc.), perchloric acid, etc., N-haloimide such as N-bromosuccinimide etc., lead tetraacetate, hydrogen peroxide or its salt (e.g. nickel peroxide, etc.), metal oxide such as mercuric oxide, manganese dioxide, nickel peroxide, etc., cupric compound (e.g. cupric acetate, cupric sulfate, etc.) and the like.

This reaction is usually carried out in a solvent such as water, acetic acid, methanol, ethanol, tetrahydrofuran, dioxane and the like and a mixture thereof, which should be appropriately selected in accordance with the kind of oxidizing agent to be used.

This reaction is usually carried out under ice-cooling to at ambient temperature, or under reflux.

As to Process 7 for Elimination of protective groups (i.e. Process 7-1, Process 7-2 and Process 7-3), it is to be noted that, in case that acyl for R$^1$ and acyl moiety of acylamino for $R_a^3$ has one or more protective groups for hydroxy, amino and (or) carboxy, such protective groups also may be simultaneously removed in this process or such protective group(s) may be removed by subjecting additionally the reaction product to removal reaction of this process (i.e. Processes 7-1, 7-2 and 7-3) and such a case is included within the scope of this process.

Preparation of Starting Compounds (II) and (III)

The starting compounds (II) and (III) including new compound can be prepared by methods as follows.

(1) Process 1$^s$

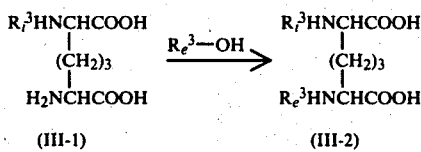

(2) Process 2$^s$

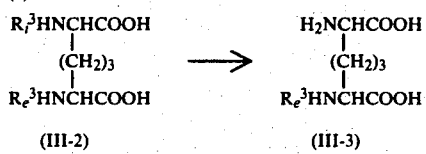

(3) Process 3$^s$

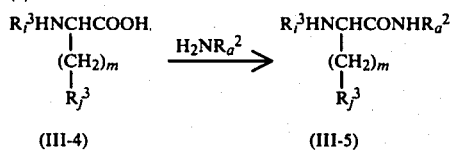

(4) Process 4$^s$

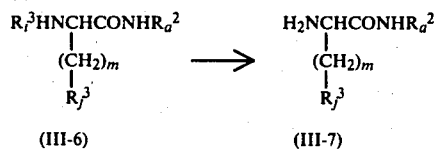

(5) Process 5$^s$

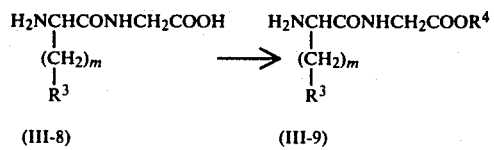

(6) Process 6$^s$

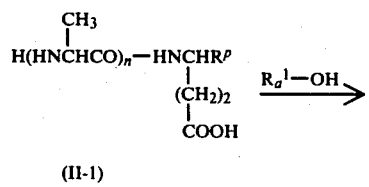

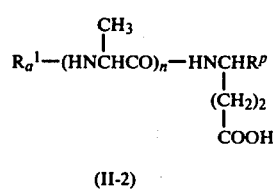

(7) Process 7$^s$

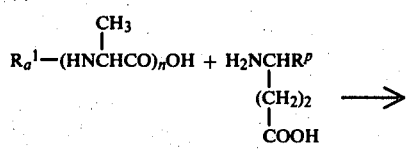

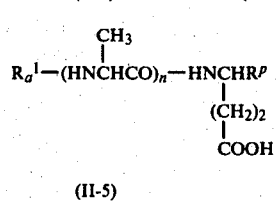

wherein $R_i^3$ is an amino protective group, $R_j^3$ is the same as that of $R^3$ excepting carboxy, $R^4$ is an ester forming group, and $R_e^3$, $R_a^2$, $R^3$, $R_a^1$, m and n are each as defined above.

Preferred example of an amino protective group for $R_i^3$ is the same as illustrated for amino protective group of protected amino for $R_a^3$, $R_d^3$, Y and $R_h^3$.

Preferred example of an ester forming group for $R^4$ is the same as that exemplified in the explanation of protected carboxy for $R^2$.

(1) Process 1$^s$:

Compound (III-1) $\xrightarrow{R_e^3-OH}$ Compound (III-2)

This process relates to a method for preparing Compound (III-2) by reacting Compound (III-1) with an acylating agent.

The acylating agent to be used in this reaction is the same as illustrated in the explanation of Process 4.

This reaction is carried out in substantially the same manner as that of Process 4.

(2) Process 2$^s$:

Compound (III-2)→Compound (III-3)

This process relates to a method for preparing Compound (III-3) by subjecting Compound (III-2) to removal reaction of an amino protective group for $R_i^3$.

The reaction is carried out in substantially the same manner as that of Process 3.

(3) Process 3$^s$:

Compound (III-4)→Compound (III-5)

This process relates to a method for preparing Compound (III-5) by reacting Compound (III-4) or its salt or its reactive derivative at the carboxy with Compound of the formula: $H_2NR_a^2$ (wherein $R_a^2$ is as defined above) or its salt or its reactive derivative.

The reaction is carried out in substantially the same manner as that of Process 1.

(4) Process 4$^s$:

Compound (III-6)→Compound (III-7)

This process relates to a method for preparing Compound (III-7) by subjecting Compound (III-6) to removal reaction of an amino protective group for $R_i^3$.

The reaction is carried out in substantially the same manner as that of Process 3.

(5) Process 5$^s$:

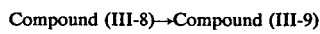
Compound (III-8)→Compound (III-9)

This process relates to a method for preparing Compound (III-9) by reacting Compound (III-8) or its salt or its reactive derivative at the carboxy with an esterifying agent.

An esterifying agent to be used in this reaction may include a conventional one such as an alcohol (e.g. methanol, ethanol, propanol, benzylalcohol, etc.) or its reactive equivalent (e.g. halide, sulfate, aliphatic or aromatic sulfonate or the corresponding diazo compound etc.) and the like.

The reaction is carried out in a conventional manner and in case of using alcohol as an esterifying agent, the reaction is usually carried out in the presence of an acid such as hydrochloric acid, sulfuric acid, methanesulfonic acid or the like, and in case of using alkyl halide as an esterifying agent, the reaction is usually carried out in the presence of a base as illustrated in the aforementioned Process 3.

(6) Process 6$^s$:

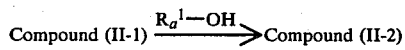
Compound (II-1) $\xrightarrow{R_a{}^1-OH}$ Compound (II-2)

This process relates to a method for preparing Compound (II-2) by reacting Compound (II-1) with an acylating agent.

The acylating agent to be used in this reaction is the same as illustrated in the explanation of Process 4.

The reaction is carried out in substantially the same manner as that of Process 4.

(7) Process 7$^s$:

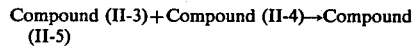
Compound (II-3)+Compound (II-4)→Compound (II-5)

This process relates to a method for preparing Compound (II-5) by reacting Compound (II-3) or its salt or its reactive derivative at the carboxy with Compound (II-4) or its salt or its reactive derivative at the carboxy.

The reaction is carried out in substantially the same manner as that of Process 1.

As to the object compound (I) and starting compounds (II) and (III) which are prepared according to the aformentioned Processes, it is to be noted that each of said compounds includes one or more stereoisomers which is due to the asymmetric carbon atoms in their molecule and all of such isomers are included within the scope of this invention.

The new peptide (I) and its pharmaceutically acceptable salts of this invention have been found to possess enhancing activities of immune response (i.e. enchancing activities of cellular immunity and humoral antibody production) and reticuloendotherial system, enhancing activity of blood stream of carbon, mitogenic activity and protective efficacy in experimental infection.

Accordingly, the new peptide (I) and its pharmaceutically acceptable salts are useful for the therapeutic treatment of infectious diseases caused by pathogenic microorganism, especially gram-negative bacteria and gram-positive bacteria and fungi.

Further, Compounds (II) and (III) are useful as intermediate for preparing Compound (I) having biologically active properties as mentioned above.

For the purpose of showing pharmaceutical utility of the new peptide (I), pharmacological test data thereof are illustrated in the following.

1. BLOOD STREAM CLEARANCE OF CARBON

Reagents.

1. Carbon suspension. Rotoring drawing ink (170 mg carbon/ml.) was diluted to 1/5 of the original concentration in saline containing 1% gelatin.

2. 0.1% aqueous sodium carbonate solution.

Procedure.

Mice (DDY male 5–6 W) were injected via the tail vein with a dose of 0.01 ml/g body weight of carbon.

Blood samples were taken by means of a pointed capillary pippet calibrated to hold a 50 $\mu$l and previously washed in heparin. This was plunged into the retroorbital venous sinus at the nasal angle of the eye. The samples were removed at 3 and 6 min. The blood was immediately discharged into 3.0 ml. of the sodium carbonate solution. This hemolyzed the blood and allowed the quantitation of carbon. The samples were then read in a spectrophotometer at 660 nm, the log concentration being obtained from a previously determined standard curve. The clearance value K may be determined by plotting log carbon concentration against time according to the following relationship;

$$K = \frac{(\log C_1 - \log C_2)}{T_2 - T_1}$$

in which $T_1$ and $T_2$ represent the time in min when the sample were withdrawn and $C_1$ and $C_2$ represent the concentrations of carbon in the blood at the time $T_1$ and $T_2$, respectively.

EXAMINATION OF EFFECT OF TEST COMPOUND ON CARBON CLEARANCE

The aqueous solution of the drug as given was administered subcutaneously to mice. Twenty four hours later, blood stream clearance of carbon was measured. K value obtained with treated mice was compared with that of control mice. The test results are shown in Table 1.

TABLE 1

| Test Compound (Example No.) | Dose (mg/mouse) | K treated/K control | *Reference Compound |
|---|---|---|---|
| Example 3 | 100 | 2.9 | — |
| (Step 2) | 1 | 1.8 | 1.8 |
| Example 5 | 100 | 1.2 | — |
| (Step 3) | 1 | 0.7 | 1.3 |
| Example 8 | 100 | 3.0 | — |
|  | 1 | 2.0 | 2.2 |
| Example 11 | 100 | 1.3 | — |
| (Step 3) | 1 | 0.9 | 1.3 |
| Example 12 | 100 | 1.7 | — |
| (Step 3) | 1 | 1.0 | 2.4 |
| Example 13 | 100 | 1.6 | — |
| (Step 2) | 1 | 0.6 | 1.8 |
| Example 14 | 100 | 1.6 | — |
| (Step 2) | 1 | 1.9 | 1.8 |
| Example 7 | 100 | 2.4 | 2.4 |

TABLE 1-continued

| Test Compound (Example No.) | Dose (mg/mouse) | K treated/K control | *Reference Compound |
|---|---|---|---|
| (Step 2) | 0.1 | 1.8 | 2.0 |

Note *Reference compound means the following compound.

$$\underset{(D)}{CH_3\underset{|}{C}HCONH\underset{|}{C}HCONHCHCOOH} \quad \underset{(L)}{\overset{OH}{|}} \quad \underset{|}{\overset{CH_3}{|}} \quad (D)$$

with side chain:
$CH_2$—$CH_2$—(L)—CONHCHCONHCH$_2$COOH—$CH_2$—$CH_2$—$CH_2$—H$_2$NCHCOOH (D)

2. PROTECTIVE EFFICACY IN EXPERIMENTAL INFECTION IN MICE

In determining the protective efficacy against experimental infections in mice, the test compound was dissolved in and diluted with sterile saline to provide prescribed concentrations of drug.

Male ICR-strain mice, aged 4 weeks were used in groups of ten mice. E. coli 22 was cultivated overnight at 37° C. on trypticase soy agar and then were suspended in a sterile saline to obtain microbial cell concentration of $9.0 \times 10^7$ CFU/ml. Mice were inoculated intraperitoneally with 0.2 ml of the suspension. Each of the test drugs was given intraperitoneally in various doses to a group of ten mice 24 hours before challenge.

Survival percent were found from the number of the surviving animals after four days of injection. Results are shown in Table 2.

TABLE 2

| Test Compound (Example No.) | Survival (%) Dose 10 mg/kg | Dose 1 mg/kg |
|---|---|---|
| Example 1 (Step 3) | 87.5 | 50.0 |
| Example 5 (Step 3) | — | 75.0 |
| Example 8 | 100.0 | 62.5 |
| Example 13 (Step 2) | 100 | 100 |
| Example 15 (Step 2) | 87.5 | 100 |

3. MITOGENIC ACTIVITIES FOR MOUSE SPLEEN CELLS

[Materials and Methods]

(1) Animal: Mice used for this experiment were female BALB/C strain, aged 9 weeks.

(2) Tissure Culture Medium: The tissure culture medium employed was a complete medium designated Roswell Park Memorial Institute (RPMI)-1640. All media employed contained 100 units/ml of penicillin G and 100 μg/ml of streptomycin sulfate and 10% fetal calf serum.

(3) Cell Preparation: Spleens were removed under sterile conditions, and washed with Hanks solution and then teased in the tissue culture medium. The cells were suspended in the tissue culture medium to contain $8 \times 10^6$ cells/ml.

(4) Culture Conditions:

Into each hole of Microtest II tissue culture plate ($8 \times 12$ hole) (maker: Falcon Plastics Co.) were poured 0.1 ml of the above cells suspension and 0.1 ml of the prescribed concentrate of the test compound as described below and then the cultures were incubated intriplicate at 37° C. in a humidified atmosphere (95% air, 5% $CO_2$) for 48 hours.

The control culture contained 0.1 ml of the culture medium instead of the medium containing the test compound.

(5) [3H] Thymidine uptake: In all tests, 20 μl of 10 micro-curine (μ Ci)/ml of tritiated thymidine (3H-thymidine) was added to each hole for the final 24 hours of culture. After the culture was completed, the resultant cells were filtered with a filter paper, Whatman GF83 and washed successively with saline and with 5% trichloroacetic acid. The filter paper was dried and placed in a scintillator (toluene 1 l containing 0.1 g of p-bis[5-phenyloxazoyl]benzene and 4 g of 2,5-diphenyloxazoyl), and 3H-thymedine incorporated into DNA was measured.

(6) Stimulation Index:

TABLE 3

$$\text{Stimulation Index} = \frac{\text{3H-thymidine uptake(net cpm) at treatment}}{\text{3H-thymidine uptake(net cpm) at control}}$$

| Test Compound (Example No.) | Concentration (μg/ml) | 3H-thymidine uptake net cpm: av + S.E | Stimulation Index |
|---|---|---|---|
| Example No. 1 (Step 3) | 100 | 1,966 ± 100 | 4.3 |
|  | 10 | 757 ± 21 | 1.7 |
| Example No. 8 | 100 | 2,031 ± 118 | 4.5 |
|  | 10 | 1,012 ± 85 | 2.2 |
| Example No. 9 (Step 2) | 100 | 1,233 ± 108 | 2.7 |
|  | 10 | 656 ± 6 | 1.5 |
| Control |  | 452 ± 30 | 1.0 |

4. ENHANCING ACTIVITIES OF CELLULAR IMMUNITY AND HUMORAL ANTIBODY PRODUCTION

Guinea pigs (groups of five) were given 0.1 ml of FIA (Freund's Incomplete Adjuvent) emulsion containing 500 μg of ovalbumin in both posterior footpads. Control groups received antigen in FIA only, whereas the test groups received the antigen with test compound in FIA. The animals were skin-tested on day 14 and bled on day 16.

The results are as the following table 4.

TABLE 4

| Test Compound (Example No.) | Dose (μg/site) | Cellular immunity[1] skin reaction (m.m diameter, M ± S.E.) | Humoral immunity hemagglutination titer (M ± S.E. $\log_2$)[2] |
|---|---|---|---|
| Example 1 (Step 3) | 0 |  | 5.8 ± 0.3 |
|  | 1 | — | 7.5 ± 0.4[3] |
|  | 10 |  | 8.2 ± 0.4[3] |
| Example 8 | 0 |  | 0 |
|  | 1 |  | 2.0 ± 1.3 |

TABLE 4-continued

| Test Compound (Example No.) | Dose (μg/site) | Cellular immunity[1] skin reaction (m.m diameter, M ± S.E.) | Humoral immunity hemagglutination titer (M ± S.E. log₂)[2] |
|---|---|---|---|
| | 10 | | 7.1 ± 1.1[3] |

Note:
[1]The skin test was performed on the back by intradermal injection of 5 μg of antigen dissolved in 0.1 ml of saline. Skin reaction of the test site was measured at 48 hours.
[2]Antibody estimation was carried out as follows: Ovalbumun-coated sheep red blood cells were prepared by chromium chloride. Antibody titer was expressed as the reciprocal of the highest dilution of serum evoking threshold hemogglutination and hemolysin. The results were converted to log₂ unit.
[3]Significance was calculated by Student's t-test; $P < 0.05$ The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily dose of about 2-100 mg. of the active ingredient/kg. of a human being or an animal is generally given for treating diseases, and an average single dose of about 50 mg., 100 mg., 250 mg., and 300 mg. is generally administered.

The following examples are given for purpose of illustrating this invention.

In the following examples, starting compounds and object compounds are expressed by using the following abbreviations:

Lac: lactoyl
Ala: Alanyl
Glu: Glutamyl
Gly: Glycyl
DAP: α,ε-Diaminopimelyl
Z: benzyloxycarbonyl
Boc: t-butoxycarbonyl
Bzl: benzyl
Me: methyl
Et: ethyl
Su: N-hydroxysuccinimide
Bzh: benzhydryl
Ac: acetyl
Val: Valyl
Tyr: Tyrosyl
Apm: α-Aminopimelyl Preparation 1

(1) Step 1

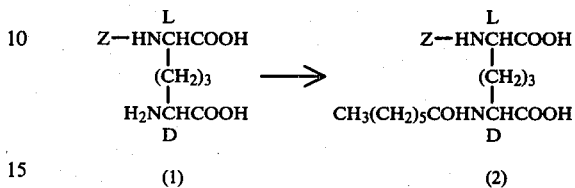

To a mixture of Z-(L)-mesoDAP(1) (0.80 g) and bis(-trimethylsilyl)acetamide in a mixture of methylene chloride (60 ml) and dimethylformamide (3 ml) was added n-heptanoic anhydride (0.65 g) and the mixture was stirred for 2 hours at room temperature. The reaction mixture was concentrated and the residue was dissolved in ethyl acetate. The solution was washed with water, dried over mangesium sulfate and evaporated to give Z-(L)-heptanoyl-(D)-mesoDAP(2) (0.82 g).

I.R. (film): 3300, 2600-2400, 1740-1620 cm⁻¹
N.M.R. (CDCl₃), δ(ppm): 0.90 (3H, t, J=7 Hz), 1.00-2.50 (16H, m), 4.10-4.80 (2H, m), 5.10 (2H, s), 7.20 (5H, s), 9.30 (2H, s)

(2) Step 2

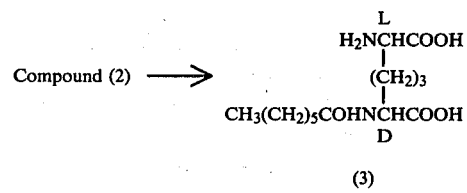

A solution of Z-(L)-n-heptanoyl-(D)-mesoDAP(2) (0.80 g) in acetic acid (40 ml) was hydrogenated over 10% palladium-charcoal (0.3 g). The catalyst was removed by filtration and the filtrate was evaporated to give an oil, which was dissolved in water (50 ml) and evaporated again to give n-heptanoyl-(D)-mesoDAP(3) (540 mg).

I.R. (Nujol): 3350, 2600-2400, 1700, 1640 cm⁻¹
N.M.R. (DMSO-d₆), δ(ppm): 0.86 (3H, t, J=7 Hz), 1.00-2.40 (16H, m), 3.30 (1H, m), 4.20 (1H, m)

Preparation 2

(1) Step 1

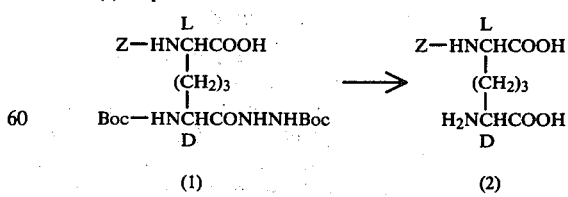

Z-(L)-Boc-(D)-mesoDAP-(D)-NHNHBoc(1) (2.26 g) was dissolved in trifluoroacetic acid (6 ml) and the solution was reacted for 15 minutes at ambient temperature. Excess trifluoroacetic acid was evaporated to give an oily residue which was dissolved in 0.1 N sulfuric acid (42 ml). The solution was cooled in an ice-bath and to the solution was added sodium periodate (1.078 g) in water (15 ml). The resulting mixture was reacted for an hour and then treated with sodium bisulfite. The resulting mixture was adjusted to pH to neutral and concentrated to about 10 ml and then adjusted to pH 2.0. The concentrate was passed through a column of a macroporous non-ionic adsorption resin, Hp 20 (100 ml) and eluted with water and a mixture of water and methanol (6:4), successively.

Evaporation of the latter fraction gave Z-(L)-mesoDAP(2) (1.0 g).

N.M.R. (DMSO-d6), δ(ppm): 1.16–2.0 (6H, broad m), 3.30 (1H broad), 3.90 (1H, broad), 5.00 (2H, s), 7.33 (5H, s)

(2) Step 2

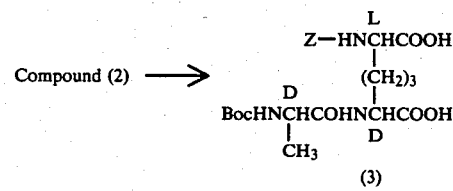

Z-(L)-mesoDAP(2) (1.50 g) was dissolved in a mixture of dioxane (30 ml), water (20 ml) and triethylamine (1.0 g). To the solution was added Boc-D-AlaOSu (1.32 g) and the resulting mixture was reacted overnight at ambient temperature. The reaction mixture was concentrated and the concentrate was acidified with dil hydrochloric acid to give precipitates. The precipitates were extracted with ethyl acetate. The extract was washed with water and dried over magnesium sulfate and then evaporated to give Z-(L)-Boc-D-Ala-(D)-mesoDAP(3) (1.90 g).

N.M.R. (DMSO-d6), δ(ppm): 1.20–2.0 (18H, m), 3.70–4.40 (3H, m), 5.00 (2H, s), 7.37 (5H, s)

(3) Step 3

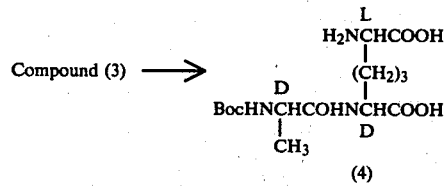

Z-(L)-Boc-D-Ala-(D)-mesoDAP(3) (1.80 g) in acetic acid (40 ml) was hydrogenated over 10% palladium black (400 mg). The catalyst was filtered off and the filtrate was evaporated to give a pasty residue. To the residue was added toluene and the solution was evaporated to give Boc-D-Ala-(D)-mesoDAP(4) (1.50 g).

N.M.R. (D2O), δ(ppm): 1.17–2.0 (18H, m), 3.30 (1H, broad), 3.80–4.30 (2H, m)

Preparation 3

(1) Step 1

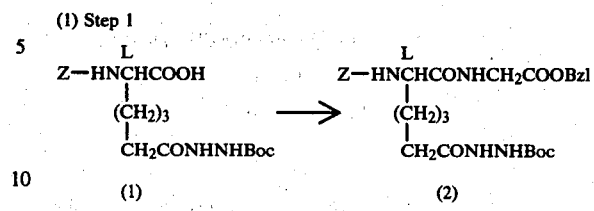

Isobutylchloroformate (0.82 g) was dissolved in methylene chloride (30 ml) and the solution was cooled to −15° C. To the solution was added dropwise a solution of Z-L-Apm(ε-NHNHBoc) (2.17 g) and triethylamine (0.61 g) in methylene chloride (20 ml) in the course of 10 minutes and the resulting mixture was reacted at the same temperature for 20 minutes. To the reaction mixture was added dropwise a solution of GlyOBzl p-toluenesulfonate (1.69 g) and triethylamine (0.51 g) in methylene chloride (20 ml) in the course of 15 minutes. The resulting mixture was reacted at the same temperature for an hour and then concentrated. The concentrate was dissolved in ethyl acetate and the ethyl acetate layer was washed with 5% sodium bicarbonate, water, dil hydrochloric acid and water, successively. The ethyl acetate layer was dried over magnesium sulfate and concentrated. The concentrate was chromatographed on silicagel (80 g) and eluted with chloroform. The fractions containing the object compound were collected and concentrated to give Z-L-Apm(ε-NHNHBoc)-GlyOBzl(2) (2.40 g).

N.M.R. (CD3OD), δ(ppm): 1.40 (9H, s), 1.34–1.75 (6H, m), 2.03–2.27 (2H, m), 3.95 (2H, s), 4.03–4.20 (1H, m), 5.05 (2H, s), 5.12 (2H, s), 7.30 (5H, s)

(2) Step 2

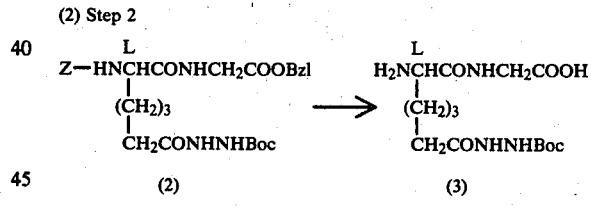

Z-L-Apm(ε-NHNHBoc)-GlyOBzl(2) (1.14 g) in a mixture (50 ml) of methanol and water (3:1) was hydrogenated over 10% palladium black (0.20 g) under 1.5 to 2 atomospheric pressure of hydrogen for 4 hours. The catalyst was filtered off and the filtrate was concentrated to give L-Apm(ε-NHNHBoc)-GlyOH(3).

Preparation 4

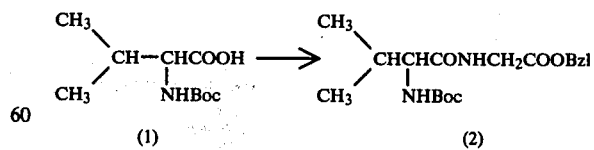

Boc-L-val-GlyOBzl(2) was prepared in substantially the same manner as step 1 of Preparation 3.

N.M.R. (CDCl3), δ(ppm): 0.90 (3H, d, J=7 Hz), 1.0 (3H, d, J=7 Hz), 1.47 (9H, s), 1.80–2.50 (1H, m), 4.10 (2H, d, J=7 Hz), 3.86–4.20 (1H, m), 5.20 (2H, s), 6.50 (1H, broad), 7.36 (5H, s).

Preparation 5

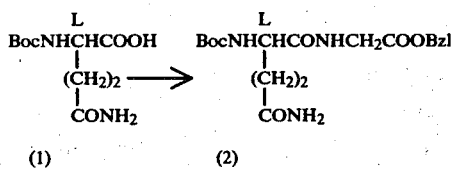

Boc-L-Glu(γ-NH₂)-GlyOBzl(2) was prepared in substantially the same manner as step 1 of Preparation 3.

N.M.R. (DMSO-d₆), δ(ppm): 1.37 (9H, s), 1.50–2.40 (4H, m), 3.92 (2H, d, J=7 Hz), 5.13 (2H, s), 6.67–7.07 (2H, broad), 7.23 (1H, broad s), 7.40 (5H, s), 8.30 (1H, t, J=7 Hz)

Preparation 6

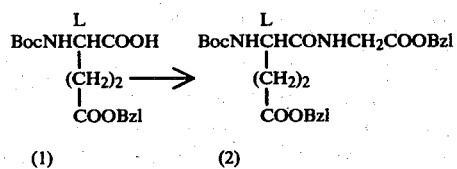

Boc-L-Glu(γ-OBzl)-GlyOBzl(2) was prepared in substantially the same manner as step 1 of Preparation 3.

N.M.R. (DMSO-d₆), δ(ppm): 1.42 (9H, s), 1.66–2.50 (4H, m), 3.98 (2H, d, J=9 Hz), 4.0–4.30 (1H, m), 5.15 (2H, s), 5.20 (2H, s), 7.43 (10H, s)

Preparation 7

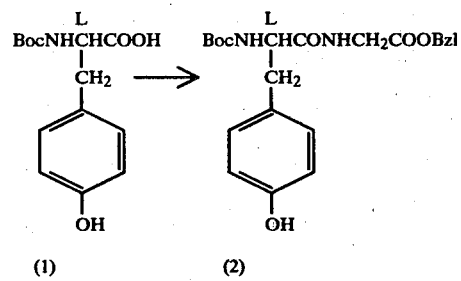

Boc-L-Tyr-GlyOBzl (2) was prepared in substantially the same manner as step 1 of Preparation 3.

Preparation 8

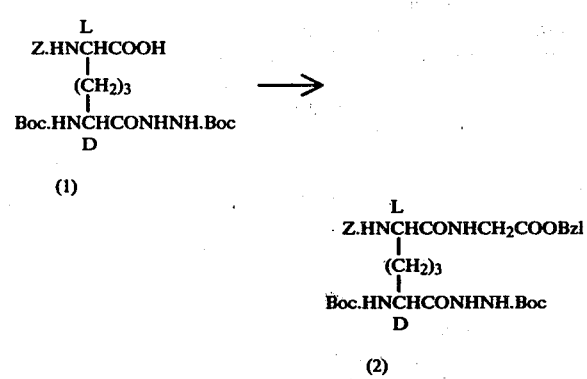

Z-(L)-Boc(D)meso-DAP(D)-NHNHBoc (1) (10.8 g) and N-methyl-morpholine (2.02 g) were dissolved in methylene chloride (110 ml) and stirred at −10°−−15° C. Isobutyl chlorocarbonate (2.73 g) was added dropwise to the solution and the mixture was stirred for thirty minutes at ambient temperature. To the solution was added dropwise a solution of glycine benzyl ester p-toluenesulfonate (6.75 g) and N-methyl morpholine (2.02 g) in methylene chloride (110 ml). The solution was stirred for two hours at −10°−−15° C. and for an hour at ambient temperature. Methylene chloride was distilled off under reduced pressure and the residue was dissolved into a mixture of ethyl acetate (150 ml) and 1% aqueous hydrochloric acid (60 ml). The ethyl acetate layer was separated and washed successively with water 2% aqueous sodium bicarbonate and aqueous sodium chloride in turn. The ethyl acetate layer was dried over anhydrous magnesium sulfate and evaporated to dryness under reduced pressure. The residue thus obtained was recrystallized from ether to give Z-(L)-Boc(D)-meso-DAP(L)GlyOBzl-(D)-NHNHBoc. (2) (12.3 g), mp. 85–87.

N.M.R. (CDCl₃), δ(ppm): 1.43 (18H, s), 1.5–2.2 (6H, m), 4.10 (2H, d, J=6 Hz), 4.1–4.5 (2H, m), 5.10 (2H, s), 5.17 (2H, s), 5.40 (1H, d, J=8 Hz), 5.90 (1H, d, J=8 Hz), 6.73 (1H, broad s), 7.33 (10H, s), 7.73 (1H, broad s), 8.4–8.6 (1H, m).

Preparation 9

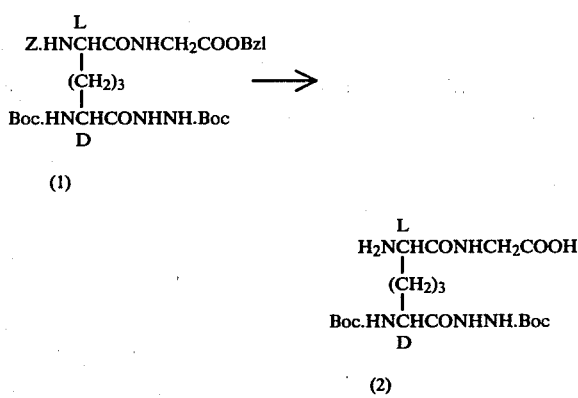

Z-(L)-Boc(D)-meso-DAP(L)-GlyoBzl-(D)-NHNHBoc (1) (12.0 g) was hydrogenated in a mixture of methanol (100 ml) and acetic acid (2.4 ml) over 10% palladium black (2 g). After completion of the reaction, the catalyst was removed by filtration and the filtrate was evaporated to dryness under reduced pressure. To the residue was added water (30 ml) and the solution was evaporated to dryness. This operation was repeated three times. The residue thus obtained was triturated with ether to give Boc(D)-meso-DAP(L)GlyOH-(D)-NHNHBoc (2) (7.80 g). mp 130°–138° C. (dec).

N.M.R. (CD₃OD), δ(ppm): 1.60 (9H, s), 1.63 (9H, s), 1.7–2.0 (6H, m), 3.92 (2H, s), 3.8–4.1 (2H, m)

Preparation 10

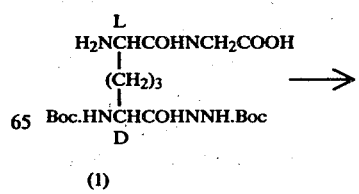

-continued

H₂NCHCOHNCH₂COOBzh   L
|
(CH₂)₃
|
Boc.HNCHCOHNNH.Boc   D (2)

p-Toluenesulfonic acid (monohydrate) (0.56 g) was added to a solution of Boc-(D)-mesoDAP-(D)-NHNHBoc-(L)-GlyOH (1) (1.39 g). To the mixture was added a solution of diphenyldiazomethane (0.62 g) in methanol (1 ml). The resulting mixture was stirred at ambient temperature for 30 minutes. To the reaction mixture was added an additional diphenyldiazomethane (0.78 g) until the starting material (1) was disappeared on thin layer chromatography. An excess of the reagent was distroyed by adding acetic acid and the mixture was adjusted to pH 8 with saturate aqueous sodium bicarbonate and then evaporated. The residue was dissolved in ether (3 ml) and triturated with n-hexane (5 ml). The solvents were removed by decantation. This operation was further repeated twice. The residue was put on a column of silica-gel (30 g) and eluted with a mixture of ethyl acetate and methanol (10:1). The fractions containing the object compound (2) were combined and evaporated to give a solid, which was purified by reprecipitation from a mixture of ether and n-hexane (1:2) to give Boc-(D)-mesoDAP-(D)-NHNHBoc-(L)-GlyOBzh (2) (1.22 g).

N.M.R. (CDCl₃), δ(ppm): 1.33 (18H, s), 1.1–1.8 (6H, m), 3.1–3.5 (1H, m), 3.9–4.3 (3H, m), 5.2–5.5 (1H, m), 6.75 (1H, s), 7.3 (10H, s), 7.6–8.0 (1H, m)

EXAMPLE 1

(1) Step 1

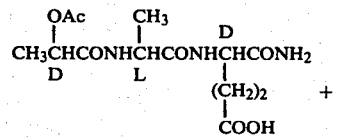

(1)

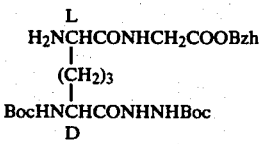

(2)

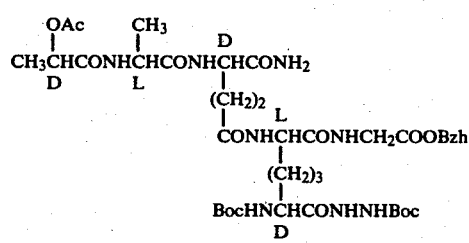

(3)

To a mixture of D-Lac-(OAc)-L-Ala-D-Glu(OH)NH₂ (1) (0.33 g) and triethylamine (0.10 g) in methylene chloride (3 ml) was added dropwise isobutyl chloroformate (0.13 g) at −23° C. to −16° C. The resulting mixture was stirred for 20 minutes at −16° C. and to the solution was added a solution of Boc-(D)-mesoDAP-(D)-NHNHBoc-(L)-GlyOBzh (2) (0.63 g) in methylene chloride (2 ml) at −25° C. to −21° C. The resulting mixture was stirred for an hour at −20° C. to −15° C. and then the temperature was raised to ambient temperature. To the reaction mixture was added water (1 ml) and the resulting mixture was concentrated. Ethyl acetate (10 ml) and 10% hydrochloric acid (5 ml) were added to the concentrate. The resulting mixture was filtered and the insoluble materials were collected and washed with water to give a solid. The solid was dissolved in methanol and the solution was triturated with ether to give D-Lac(OAc)-L-Ala-γ-D-Glu(α-NH₂)-(L)-Boc(D)-mesoDAP-(D)-NHNHBoc-(L)-GlyOBzh (3) (0.60 g).

N.M.R. (DMSO-d₆), δ(ppm): 1.39 (18H, s), 1.1–1.8 (14H, m), 2.05 (3H, s), 1.9–2.3 (2H, m), 3.8–4.4 (6H, m), 4.98 (1H, q, J=7 Hz), 6.8 (1H, s), 6.7–6.8 (1H, m), 7.05 (1H, broad), 7.35 (10H, s), 7.2–7.5 (1H), 7.8–8.0 (2H, m), 8.20 (1H, d, J=7 Hz), 8.35 (1H, broad s), 8.7 (1H, broad s), 9.55 (1H, s)

(2) Step 2

Compound (3) ⟶

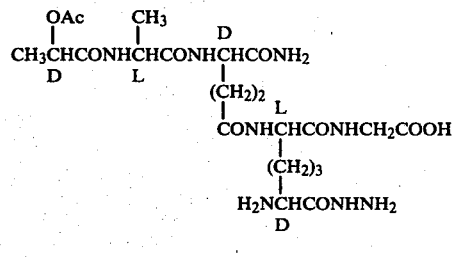

(4)

D-Lac(OAc)-L-Ala-γ-D-Glu(α-NH₂)-(L)-Boc(D)-mesoDAP-(D)-NHNHBoc-(L)-GlyOBzh (3) (0.59 g) was added to a mixture of trifluoroacetic acid (1.5 ml) and anisole (0.1 ml) and the resulting mixture was stirred for 15 minutes at ambient temperature. An additional trifluoroacetic acid (1 ml) was added to the reaction mixture, and the resulting mixture was stirred for 15 minutes. After evaporation of trifluoroacetic acid, the residue obtained was pulverized with ether to give D-Lac(OAc)-L-Ala-γ-D-Glu(α-NH₂)-(L)-mesoDAP-(D)-NHNH₂-(L)-GlyOH (trifluoroacetic acid salt) (4) (0.54 g).

N.M.R. (D₂O), δ(ppm): 1.41 (3H, d, J=7 Hz), 1.50 (3H, d, J=7 Hz), 1.3 to 1.7 (2H, m), 1.7 to 2.1 (4H, m), 2.18 (3H, s), 2.1 to 2.2 (2H, m), 2.3 to 2.5 (2H, m), 4.01 (2H, s), 4.1 to 4.4 (4H, m), 5.02 (1H, q, J=7 Hz)

(3) Step 3

Compound (4) ⟶

-continued

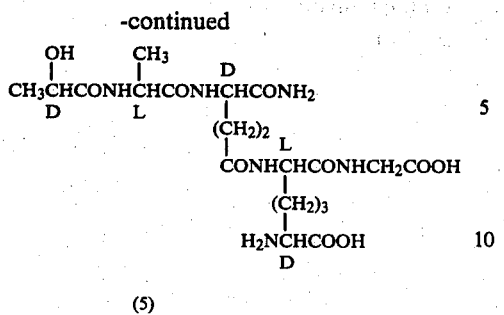

(5)

To a solution of D-Lac(OAc)-L-Ala-γ-D-Glu(α-NH₂)-(L)-mesoDAP-(D)-NHNH₂-(L)-GlyOH (4) (0.54 g) in a mixture of methanol (1 ml) and water (5 ml) was added 1 M potassium carbonate (2 ml). The resulting mixture was stirred for four hours at ambient temperature and then an additional 1 M potassium carbonate (0.2 ml) was added thereto. The resulting mixture was stirred for two hours at the same temperature, cooled to 0° C. and adjusted to pH 1 with 1 N sulfuric acid. To the mixture was added a solution of sodium periodate (0.15 g) in water (1.5 ml) and the resulting mixture was stirred for 35 minutes at the same temperature. Sodium bisulfite (0.18 g) was added to the reaction mixture, which was adjusted to pH 3 with 1 M potassium carbonate and evaporated. To the residue were added methanol (2 ml) and water (0.5 ml) and insoluble materials were filtered off. The filtrate was concentrated and the concentrate was dissolved in water (1.5 ml) and the solution was adjusted to pH 2.8 with 1 N hydrochloric acid. The solution was passed through a column packed with macroporous non-ionic adsorption resin, Hp 20 and eluted with water. The fractions containing the object compound (5) were combined and concentrated. The concentrate was recrystallized from water to give D-Lac-L-Ala-γ-D-Glu(α-NH₂)-(L)-mesoDAP-(L)-GlyOH (5) (0.22 g).

N.M.R. (D₂O), δ(ppm): 1.38 (3H, d, J=7 Hz), 1.41 (3H, d, J=6 Hz), 1.3 to 1.7 (2H, m), 1.7 to 2.2 (6H, m), 2.3 to 2.5 (2H, m), 3.75 (1H, t, J=6 Hz), 3.90 (2H, s), 4.2 to 4.4 (4H, m)

EXAMPLE 2

(1) Step 1

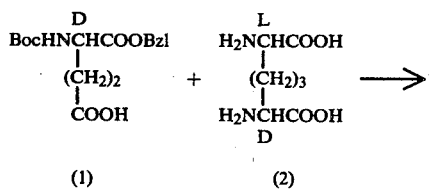

-continued

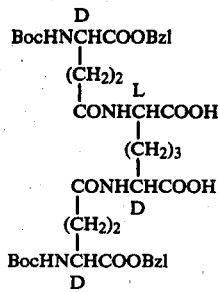

(3)

To a solution of Boc-D-Glu(OH)OBzl (1) (3.23 g) and triethylamine (1.01 g) in methylene chloride (40 ml) was added isobutylchloroformate (1.36 g) at −10° to −15° C. The resulting mixture was stirred for an hour at the same temperature. To the reaction mixture was added a solution of mesoDAP (2) trimethylsilylester which was prepared by reacting mesoDAP(2) (0.95 g), bis(trimethylsilyl)acetamide (10 ml) and dimethylformamide (5 ml) in methylene chloride (10 ml) with stirring overnight at ambient temperature. The resulting mixture was stirred for 1.5 hours at −10° to −15° C. and evaporated in vacuo. The residue was dissolved in a mixture of ethyl acetate (50 ml) and 2.5% hydrochloric acid (50 ml). The organic layer was washed with 2.5% hydrochloric acid (50 ml) and water (50 ml) and dried over magnesium sulfate. The solvent was distilled off and the residue was triturated with isopropylether (30 ml) and the precipitate was filtered and washed with isopropylether to give bis(γ-Boc-D-Glu(α-OBzl))-mesoDAP (3) (3.5 g).

N.M.R. (CDCl₃), δ(ppm): 1.33 (18H, s), 1.0 to 2.5 (14H, m), 4.0 to 4.7 (4H, m), 5.10 (4H, s), 7.30 (10H, s)

(2) Step 2

Compound (3) ⟶ 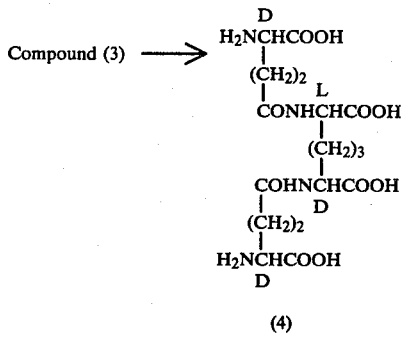

(4)

A solution of bis(γ-Boc-D-Glu(α-OBzl))-mesoDAP (3) (1.20 g) in a mixture of methanol (20 ml) and water (5 ml) was hydrogenated over 10% palladium black (0.3 g). The reaction was completed (about for three hours), the catalyst was filtered off and the filtrate was evaporated to dryness in vacuo. The residue was dissolved in trifluoroacetic acid (5 ml) and the solution was stirred for 15 minutes at ambient temperature. Trifluoroacetic acid was distilled off and the residue was dissolved in water (5 ml) and the solution was adjusted to pH 3.0 with 1 N sodium hydroxide and passed through a column packed with macroporous non-ionic adsorption resin, Hp (20 (100 ml). Elution was carried out with water and the eluate was concentrated. The concentrate was lyophilized to give bis(γ-D-Glu(α-OH))-mesoDAP (4) (0.60 g).

I.R. (Nujol): 2300–3500, 1720, 1640 cm$^{-1}$

N.M.R. (D$_2$O), δ(ppm): 1.2 to 2.8 (14H, m), 4.00 (2H, t, J=5 Hz), 4.35 (2H, t, J=6 Hz)

EXAMPLE 3

(1) Step 1

```
         D                              L
CH3(CH2)5CONHCHCOOBzl        HCl.H2NCHCOOMe
         |                            |
        (CH2)2            +          (CH2)3          ──→
         |                            |
         COOSu                HCl.H2NCHCOOMe
                                      D
         (1)                         (2)
```

```
              D
CH3(CH2)5CONHCHCOOBzl
              |
             (CH2)2
              |
              L
              CONHCHCOOMe
              |
             (CH2)3
              |
              COHNCHCOOMe
              |    D
             (CH2)2
              |
CH3(CH2)5COHNCHCOOBzl
              D (3)
```

Bis(heptanoyl-γ-D-Glu(α-OBzl)-mesoDAP (diOMe) (3) was prepared in substantially the same manner as step 1 of Example 2 from compounds (1) and (2).

N.M.R. (CD$_3$OD), δ(ppm): 0.83 (6H, t, J=5 Hz), 1.0 to 2.5 (34H, m), 3.62 (6H, s), 4.2 to 4.6 (4H, m), 5.08 (4H, s), 7.27 (10H, s)

(2) Step 2

```
                           D
Compound (3) ──→ CH3(CH2)5CONHCHCOOH
                           |
                          (CH2)2
                           |
                           L
                           CONHCHCOONa
                           |
                          (CH2)3
                           |
                           COHNCHCOONa
                           |    D
                          (CH2)2
                           |
             CH3(CH2)5COHNCHCOOH
                           D (4)
```

Bis(heptanoyl-γ-D-Glu(α-OH)-mesoDAP (di sodium salt) (4) was prepared in substantially the same manner as step 2 of Example 2 from compound (3).

N.M.R. (D$_2$O), δ(ppm): 0.83 (6H, t, J=7 Hz), 1.0 to 2.5 (34H, m), 4.10 (4H, m)

EXAMPLE 4

(1) Step 1

```
      D                        L
Z—HNCHCOOBzl      +     H2NCHCOOH
      |                        |
     (CH2)2                  (CH2)3             ──→
      |                        |
      COOSu           CH3(CH2)5COHNCHCOOH
                                   D
      (1)                        (2)
```

```
                D
         Z—HNCHCOOBzl
                |
               (CH2)2
                |
                L
                COHNCHCOOH
                |
               (CH2)3
                |
      CH3(CH2)5COHNCHCOOH
                       D (3)
```

To a mixture of n-heptanoyl-(D)-mesoDAP (2) (0.56 g) and triethylamine (0.40 g) in 50% aqueous dioxane (40 ml) was added Z-D-Glu(γ-OSu)OBzl (1) (0.87 g) and the mixture was left overnight at room temperature. The reaction mixture was concentrated and the resulting aqueous solution was acidified with diluted hydrochloric acid and extracted with ethyl acetate. The extract was washed with water, dried over magnesium sulfate and evaporated to give Z-γ-D-Glu(α-OBzl)-(L)-n-heptanoyl-(D)-mesoDAP (3) (1.15 g).

N.M.R. (DMSO-d$_6$), δ(ppm): 0.83 (3H, t, J=7 Hz), 1.00–2.50 (20H, m), 4.0–4.30 (3H, m), 5.00 (2H, s), 5.10 (2H, s), 7.30 (10H, s)

(2) Step 2

```
                       D
Compound (3) ──→ H2NCHCOOH
                       |
                      (CH2)2
                       |
                       L
                       COHNCHCOOH
                       |
                      (CH2)3
                       |
           CH3(CH2)5COHNCHCOOH
                              D (4)
```

A solution of Z-γ-D-Glu(α-OH)-(L)-n-heptanoyl-(D)-mesoDAP (3) (0.80 g) in acetic acid (40 ml) was hydrogenated over 10% palladium-charcoal (0.3 g). The catalyst was removed by filtration and the filtrate was evaporated to give an oil, which was dissolved in water (50 ml) and evaporated again to give γ-D-Glu(α-OH)-(L)-n-heptanoyl-mesoDAP (4) (540 mg).

I.R. (Nujol): 3350, 2600–2400, 1700, 1640 cm$^{-1}$

N.M.R. (DMSO-d$_6$), δ(ppm): 0.86 (3H, t, J=7 Hz), 1.00–2.40 (16H, m), 3.30 (1H, m), 4.20 (1H, m)

EXAMPLE 5

(1) Step 1

-continued

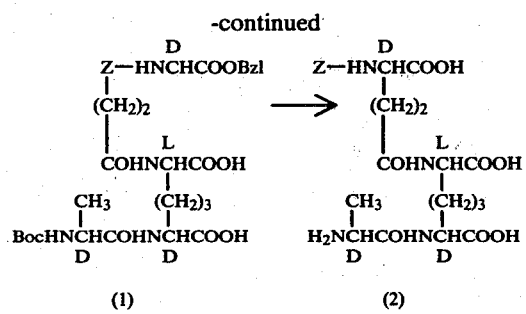

(1) → (2)

To a solution of Z-γ-D-Glu(α-OBzl)-(L)-Boc-D-Ala-(D)-mesoDAP (1) (1.0 g) in 50% aqueous methanol was added 1 N sodium hydroxide (4.2 ml) and the mixture was stood for 1 hour at room temperature. The reaction mixture was evaporated and the residue was dissolved in trifluoroacetic acid (8 ml). After standing for 15 minutes at room temperature, trifluoroacetic acid was removed by evaporation to give an oil, which was dissolved in water (10 ml) and applied to a column of Hp 20 (80 ml). The column was washed with water and eluted with methanol-water (3:7). The eluate was concentrated and lyophillized to give Z-γ-D-Glu(α-OH)-(L)-D-Ala-(D)-mesoDAP (2) (0.40 g).

I.R. (Nujol): 3300, 2600–2400, 1720–1650 cm$^{-1}$

N.M.R. (D$_2$O), δ(ppm): 1.20–2.60 (10H, m), 1.54 (3H, d, J=7 Hz), 4.0–4.20 (4H, m), 5.08 (2H, s), 7.36 (5H, s)

(2) Step 2

Compound (2) ⟶

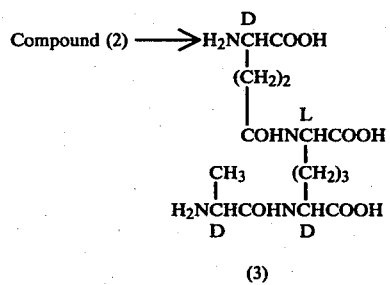

(3)

A solution of Z-γ-D-Glu(α-OH)-(L)-D-Ala-(D)-mesoDAP (2) was hydrogenated over 10% palladium-charcoal (0.2 g). After removal of the catalyst by filtration, the filtrate was concentrated to about 5 ml and lyophillized to give γ-D-Glu(α-OH)-(L)-D-Ala-(D)-mesoDAP (3) (0.24 g).

I.R. (Nujol): 3200 (shoulder), 2600–2400, 1650 cm$^{-1}$

N.M.R. (D$_2$O), δ(ppm): 1.54 (3H, d, J=7 Hz), 1.20–2.60 (10H, m), 3.80 (1H, t, J=7 Hz), 4.0–4.36 (3H, m)

EXAMPLE 6

(1) Step 1

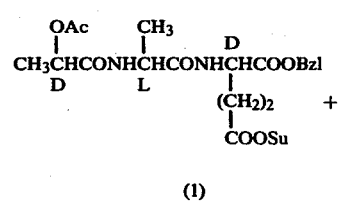

-continued

L
H$_2$NCHCONHCH$_2$COOH
|
(CH$_2$)$_3$           ⟶
|
CH$_2$CONHNHBoc (2)

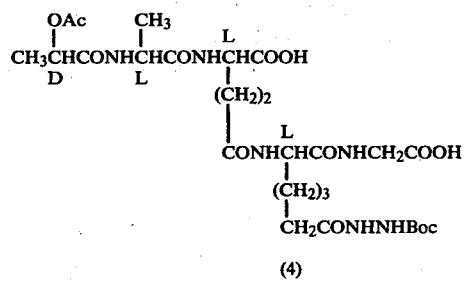

(3)

D-Lac(OAc)-L-Ala-γ-D-Glu(α-OBzl)-L-Apm(ε-NHNHBoc)-GlyOH (3) was prepared in substantially the same manner as step 1 of Example 1 from Compounds (1) and (2).

N.M.R. (CD$_3$OD), δ(ppm): 1.45 (9H, s), 1.35 (3H, d, J=7 Hz), 1.33 to 1.83 (8H, m), 2.09 (3H, s), 2.20 to 3.30 (4H, m), 2.92 (2H, s), 4.17 to 4.58 (4H, m), 5.17 (2H, s), 7.33 (5H, s)

(2) Step 2

Compound (3) ⟶

OAc     CH$_3$
|       |         L
CH$_3$CHCONHCHCONHCHCOOH
 D       L        |
                  (CH$_2$)$_2$
                  |
                  L
                  CONHCHCONHCH$_2$COOH
                  |
                  (CH$_2$)$_3$
                  |
                  CH$_2$CONHNHBoc (4)

A solution of D-Lac(OAc)-L-Ala-γ-D-Glu(α-OBzl)-L-Apm(ε-NHNHBoc)-GlyOH (3) (1.0 g) in a mixture of methanol and water (3:1) (30 ml) was hydrogenated over 10% palladium black (0.1 g) under 1.5 to two atmospheric pressure of hydrogen for 4 hours at ambient temperature. The catalyst was filtered off and the filtrate was concentrated to give D-Lac(OAc)-L-Ala-γ-D-Glu(α-OH)-L-Apm(ε-NHNHBoc)-GlyOH (4) (0.72 g).

N.M.R. (CD$_3$OD), δ(ppm): 1.40 (3H, d, J=7 Hz), 1.50 (9H, s), 1.33 to 1.83 (8H, m), 2.13 (2H, s), 2.27 to 2.33 (4H, m), 3.97 (2H, s), 4.23 to 4.58 (4H, m)

(3) Step 3

Compound (4) ⟶

-continued

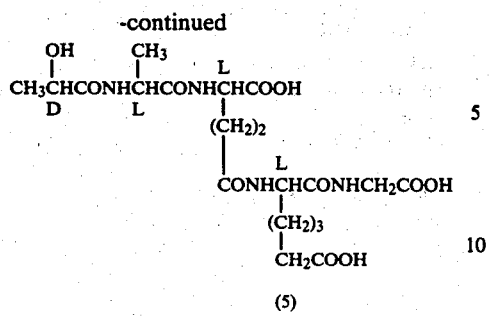

(5)

D-Lac(OAc)-L-Ala-γ-D-Glu(α-OH)-L-Apm(ε-NHNHBoc)-GlyOH (4) (0.60 g) was dissolved in a mixture of methanol and water (2:1) (10 ml), and 1 N sodium hydroxide (2.3 ml) was added thereto at 5° C. The mixture was reacted for 1.5 hours at the same temperature and concentrated in vacuo. To the concentrate was added dil hydrochloric acid to adjust to pH 1. The resulting mixture was extracted with ethyl acetate and the ethyl acetate layer was washed with saturated aqueous sodium chloride, dried over magnesium sulfate and then concentrated to give an oil. To the oil was added a cooled (5° to 10° C.) trifluoroacetic acid (5 ml) and the mixture was reacted for 30 minutes at 5° C. The reaction mixture was concentrated in vacuo and the residue was dissolved in water. To the solution was added 1 N sulfuric acid (0.7 ml), and then sodium periodate (0.16 g) was added dropwise thereto in the course of 20 minutes under ice-cooling with stirring. The reaction mixture was further reacted for 20 minutes and sodium bisulfite was added thereto until the yellow brown was disappeared. The reaction mixture was adjusted to pH 3.0 to 3.2 with 1 N sodium bicarbonate and then concentrated in vacuo to about 2 ml. The concentrate was passed through a column packed with macroporous non-ionic adsorption resin, Hp 20 (100 ml) and eluted with water. The fractions containing the object compound (5) were collected and concentrated and the concentrate was pulverized with acetone. The powder was washed with acetone and dried over magnesium sulfate to give D-Lac-L-Ala-γ-D-Glu(α-OH)-L-Apm-GlyOH (5) (0.17 g).

N.M.R. (D₂O), δ(ppm): 1.38 (3H, d, J=7 Hz), 1.42 (3H, d, J=7 Hz), 1.33 to 1.92 (8H, m), 2.20 to 2.40 (4H, m), 3.93 (2H, s), 4.10 to 4.50 (4H, m)

EXAMPLE 7

(1) Step 1

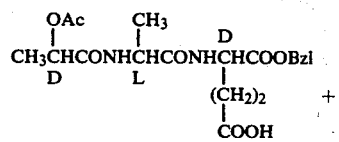

(1)

-continued

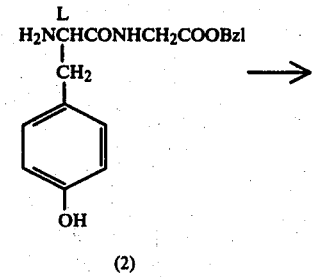

(2)

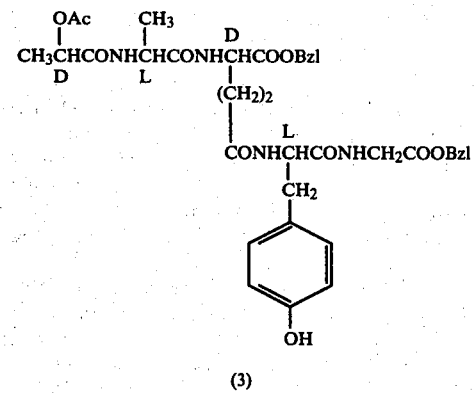

(3)

Isobutylchlorocarbonate (0.62 g) was dissolved in methylene chloride (40 ml) and the solution was cooled to −15° to −10° C., and triethylamine (0.46 g) and a solution of D-Lac(OAc)-L-Ala-D-Glu(OH)OBzl (1) (1.90 g) in methylene chloride (20 ml) were added dropwise thereto in the course of 7 minutes. The reaction mixture was reacted for 20 minutes at the same temperature and then a solution of L-Tyr-GlyOBzl (2) (1.20 g) and triethylamine (0.57 g) in methylene chloride (30 ml) was added dropwise thereto in the course of 15 minutes. The resulting mixture was reacted for 2 hours at the same temperature and concentrated. The concentrate was extracted with ethyl acetate. The ethyl acetate layer was washed successively with 5% sodium bicarbonate, water, dil hydrochloric acid and water, and then dried over magnesium sulfate. Then, the ethyl acetate layer was concentrated and the concentrate was crystallized from acetate and ether to give D-Lac-(OAc)-L-Ala-γ-D-Glu(α-OH)-L-Tyr-GlyOBzl (3) (1.97 g).

N.M.R. (CD₃OD), δ(ppm): 1.30 (3H, d, J=7 Hz), 1.40 (3H, d, J=7 Hz), 2.00 (3H, s), 2.00 to 2.17 (4H, m), 2.67 to 3.03 (2H, m), 4.00 (2H, s), 4.13 to 4.63 (4H, m), 5.13 (4H, s), 6.68 (2H, d, J=9 Hz), 7.07 (2H, d, J=9 Hz), 7.35 (10H, s)

(2) Step 2

Compound (3) ⟶

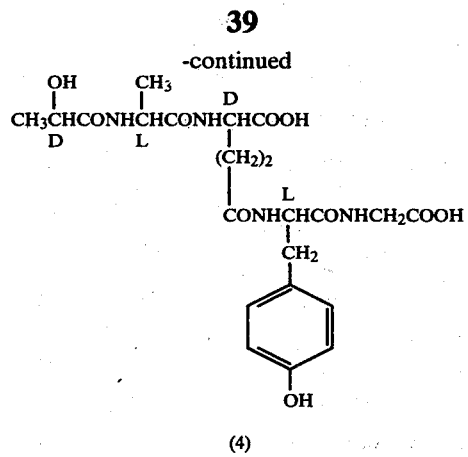

(4)

D-Lac(OAc)-L-Ala-γ-D-Glu(α-OH)-L-Tyr-GlyOBzl (3) (1.49 g) was dissolved in a mixture of methanol and water (2:1) (30 ml), and 1 N sodium hydroxide (9 ml) was added under ice-cooling with stirring. The resulting mixture was reacted for 4 hours at the same temperature and for 2 hours at ambient temperature. The reaction mixture was adjusted to pH 3.0 to 3.2 with dil hydrochloric acid and concentrated to about 4 ml. The concentrate was passed through a column packed with macroporous non-ionic adsorption resin, Hp 20 (150 ml). The column was washed with water and eluted with 30% aqueous methanol. The eluate was concentrated and the concentrate was dissolved in water and lyophilized to give D-Lac-L-Ala-γ-D-Glu(α-OH)-L-Tyr-GlyOH (4) (0.75 g).

N.M.R. (D₂O), δ(ppm): 1.38 (3H, d, J=7 Hz), 1.47 (3H, d, J=7 Hz), 1.83 to 1.25 (4H, m), 2.88 to 3.12 (2H, m), 4.00 (2H, s), 4.18 to 4.63 (4H, m), 6.88 (2H, d, J=10 Hz), 7.20 (2H, d, J=10 Hz)

EXAMPLE 8

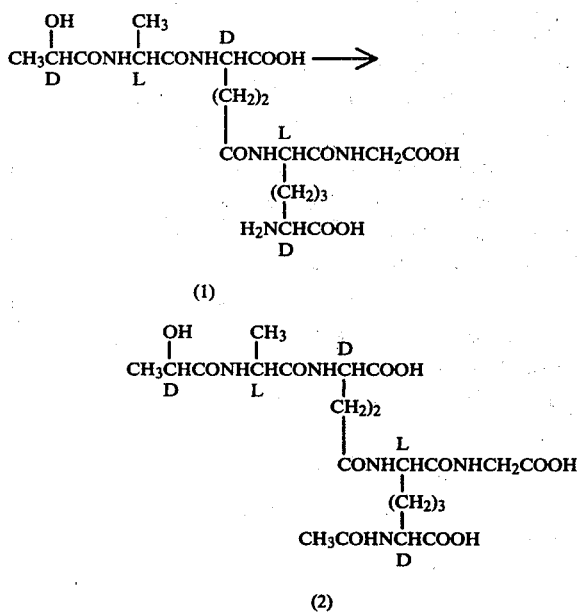

To a solution of D-Lac-L-Ala-γ-D-Glu(α-OH)-(L)-mesoDAP-(L)-GlyOH (1) (300 mg) in 50% aqueous dioxane (10 ml) was added dropwise acetyl chloride (680 mg) at 0° C. in the course of 2 hours, during which time the pH of the reaction mixture was maintained at pH 8. The reaction mixture was acidified to pH 2 and concentrated. The concentrate was dissolved in water (5 ml) and the solution was passed through a column packed with macroporous non-ionic adsorption resin, Hp 20 (30 ml). Elution was carried out with water and the eluate was concentrated. The concentrate was lyophylized to give D-Lac-L-Ala-γ-D-Glu(α-OH)-(L)-mesoDAP-(D)-acetyl-(L)-GlyOH (2) (130 mg).

N.M.R. (D₂O), δ(ppm): 1.37 (3H, d, J=7 Hz), 1.42 (3H, d, J=7 Hz), 1.3 to 2.5 (10H, m), 2.03 (3H, s), 4.00 (2H, s), 4.1 to 4.5 (5H, m)

EXAMPLE 9

(1) Step 1

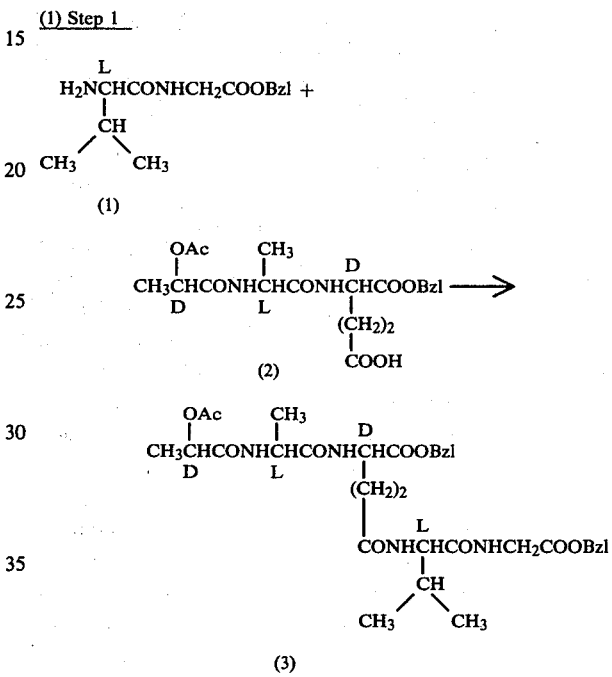

D-Lac(OAc)-L-Ala-γ-D-Glu(α-OBzl) (2) (840 mg) was dissolved in methylene chloride (40 ml) and N-methylmorpholine (200 mg) was added to the solution. The mixture was cooled in an ice-salt bath and isobutylchloroformate (270 mg) was added thereto and the resulting mixture was allowed to react for 20 minutes at −5° C.

To the reaction mixture was added L-Val-GlyOBzl (1), prepared from Boc-L-Val-GlyOBzl (5.0 g) by treatment with trifluoroacetic acid, in methylene chloride (10 ml) and the resulting mixture was stirred for an hour and concentrated. The concentrate was dissolved in ethyl acetate and the solution was washed with water and then dried over magnesium sulfate. The solvent was evaporated to give a crystalline residue which was throughly washed with ether to give D-Lac-(OAc)-L-Ala-γ-D-Glu(α-OBzl)-L-Val-GlyOBzl (3) (1.0 g).

N.M.R. (DMSO-d₆), δ(ppm): 0.82 (6H, d, J=7 Hz), 1.21 (3H, d, J=7 Hz), 1.30 (3H, d, J=7 Hz), 2.06 (3H, s), 1.50–2.50 (5H, m), 3.90 (2H, d, J=7 Hz), 4.0–4.50 (3H, m), 5.0 (1H, q, J=7 Hz), 5.13 (4H, s), 7.30 (10H, s), 7.83 (1H, d, J=7 Hz), 8.0–8.50 (3H, m)

(2) Step 2

Compound (3) ⟶

-continued

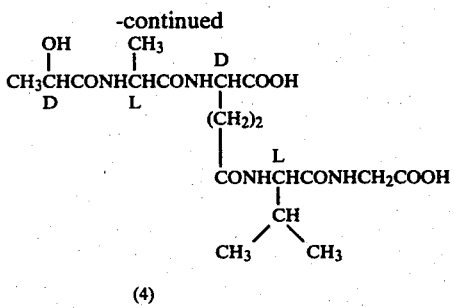

(4)

D-Lac(OAc)-L-Ala-γ-D-Glu(α-OBzl)-L-Val-GlyOBzl (3) (856 mg) was dissolved in a mixture of methanol (12 ml) and water (10 ml). To this solution was added 1 N sodium hydroxide (6 ml) and the resulting mixture was reacted for two hours at ambient temperature.

The resulting solution was concentrated and the concentrate was acidified with 1 N hydrochloric acid and then passed through a column of macroporous nonionic adsorption resin, Hp 20 (50 ml). Elution was carried out with water and methanol successively. Evaporation of the methanol fractions gave a white pasty residue which was dissolved in water and lyophillized to give D-Lac-L-Ala-γ-D-Glu(α-OH)-L-Val-GlyOH (4) (450 mg).

N.M.R. (D$_2$O), δ(ppm): 0.96 (6H, d, J=7 Hz), 1.36 (3H, d, J=7 Hz), 1.44 (3H, d, J=7 Hz), 2.0–2.60 (5H, m), 4.04 (2H, s), 4.12–4.56 (4H, m)

[α]$_D$= −42.5 (c=0.2 water)

EXAMPLE 10

(1) Step 1

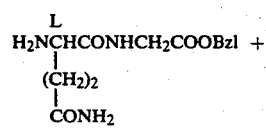

(1)

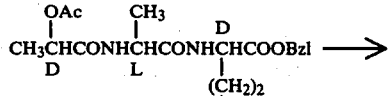

(2)

(3)

D-Lac(OAc)-L-Ala-γ-D-Glu(α-OBzl)-L-Glu(α-NH$_2$)-GlyOBzl (3) was prepared in substantially the same manner as step 1 of Example 9.

N.M.R. (DMSO-d$_6$), δ(ppm): 1.20 (3H, d, J=7 Hz), 1.26 (3H, d, J=7 Hz), 1.90–2.50 (8H, m), 2.00 (3H, s), 3.86 (2H, d, J=7 Hz), 4.0–4.50 (3H, m), 4.93 (1H, q, J=7 Hz), 5.08 (4H, s), 7.36 (10H, s)

(2) Step 2

Compound (3) ⟶

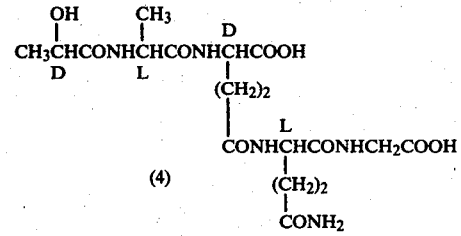

(4)

D-Lac-L-Ala-γ-D-Glu(α-OH)-L-Glu(α-NH$_2$)-GlyOH (4) was prepared in substantially the same manner as step 2 of Example 9.

N.M.R. (D$_2$O), δ(ppm): 1.36 (3H, d, J=7 Hz), 1.42 (3H, d, J=7 Hz), 1.72–2.60 (8H, m), 3.98 (2H, s), 4.12–4.52 (4H, m)

[α]$_D$= −32.5 (c=0.2 water)

EXAMPLE 11

(1) Step 1

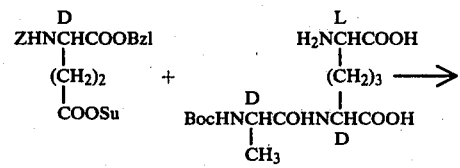

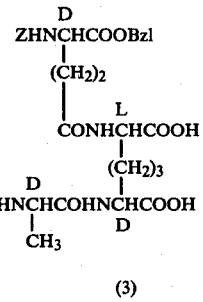

(3)

Boc-D-Ala-(D)-mesoDAP (2) (1.50 g) was dissolved in a mixture of dioxane (30 ml), water (30 ml) and triethylamine (0.85 g). To the solution was added Z-D-Glu(α-OBzl) (γ-OSu) (1) (1.95 g) and the resulting mixture was left for 24 hours at ambient temperature. The reaction mixture was concentrated, acidified with dil hydrochloric acid and extracted with ethyl acetate. The extract was washed with water, dried over magnesium sulfate and then evaporated to dryness to give Z-γ-D-Glu(α-OBzl)-(L)-Boc-D-Ala-(D)-mesoDAP (3) (2.60 g).

N.M.R. (DMSO-d$_6$), δ(ppm): 1.0–2.50 (22H, m), 3.83–4.40 (4H, m), 5.05 (2H, s), 5.15 (2H, s), 7.37 (10H, s)

(2) Step 2

Compound (3) ⟶

(2) Step 2

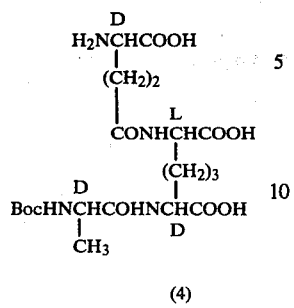

(4)

A solution of Z-γ-D-Glu(α-OBzl)-(L)-Boc-D-Ala-(D)-mesoDAP (3) (1.10 g) in acetic acid (30 ml) was hydrogenated over 10% palladium black (300 mg). The catalyst was filtered off and the filtrate was evaporated to give a pasty residue which was dissolved in water (30 ml). The aqueous solution was passed through a column of macroporous non-ionic adsorption resin, Hp 20 (80 ml) and the column was eluted with water, a mixture of methanol and water (2:8) and a mixture of methanol and water (3:7), successively. The fractions from the third solvent system were evaporated to give γ-D-Glu(α-OH)-(L)-Boc-D-Ala-(D)-mesoDAP (4) (0.80 g).

N.M.R. (DMSO-$d_6$), δ(ppm): 1.16 (3H, d, J=7 Hz), 1.44 (9H, s), 1.0–2.50 (10H, m), 3.44 (1H, broad s), 3.80–4.32 (3H, m), 6.86 (1H, d, J=7 Hz), 7.80 (1H, d, J=7 Hz), 8.20 (1H, d, J=7 Hz)

(3) Step 3

Compound (4) ⟶

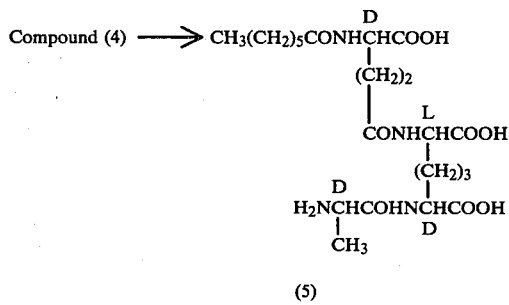

(5)

γ-D-Glu(α-OH)-(L)-Boc-D-Ala-(D)-mesoDAP (4) (740 mg) was dissolved in a mixture of methanol (20 ml) and triethylamine (460 mg). To the solution was n-heptanoic anhydride (400 mg) and the mixture was left for two hours at ambient temperature. The reaction mixture was evaporated, treated with dil hydrochloric acid and then extracted with ethyl acetate. The extract was washed with water, dried over magnesium sulfate and evaporated to give an oily residue. The residue was dissolved in trifluoroacetic acid (5 ml) and the solution was reacted for 15 minutes at ambient temperature. The reaction mixture was evaporated to dryness to give an oily residue which was dissolved in water (20 ml). The solution was passed through a column of macroporous non-ionic adsorption resin, Hp 20 (80 ml) and the column was eluted with water and a mixture of methanol and water (3:7), successively. The fractions from a mixture of methanol and water (3:7) was evaporated and lyophillized to give n-heptanoyl-γ-D-Glu(α-OH)-(L)-D-Ala-mesoDAP (5) (370 mg).

N.M.R. ($D_2O$), δ(ppm): 0.84 (3H, t, J=7 Hz), 1.0–2.60 (20H, m), 1.56 (3H, d, J=7 Hz), 4.12 (1H, q, J=7 Hz), 4.20–4.44 (3H, m)

$[α]_D = -5.0$ (c=0.2 water)

EXAMPLE 12

(1) Step 1

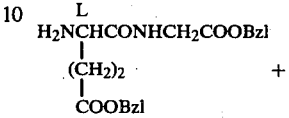

(1)

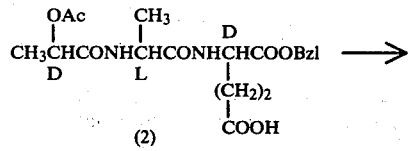

(2)

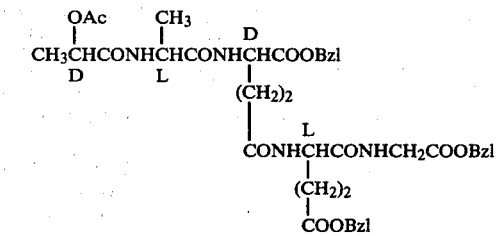

(3)

D-Lac(OAc)-L-Ala-γ-D-Glu(α-OBzl)-L-Glu(γ-OBzl)-GlyOBzl (3) was prepared in substantially the same manner as step 1 of Example 9.

N.M.R. (DMSO-$d_6$), δ(ppm): 1.23 (3H, d, J=7 Hz), 1.30 (3H, d, J=7 Hz), 1.60–2.50 (8H, m), 2.03 (3H, s), 3.93 (2H, d, J=7 Hz), 4.0–4.70 (3H, m), 5.00 (1H, q, J=7 Hz), 5.06 (2H, s), 5.12 (4H, s), 7.37 (15H, s), 7.90–8.50 (4H, m)

(2) Step 2

Compound (3) ⟶

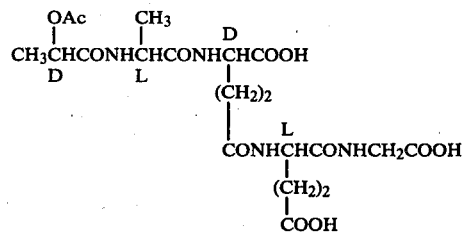

(4)

D-Lac(OAc)-L-Ala-γ-D-Glu(α-OH)-L-Glu(γ-OH)-GlyOH (4) was prepared in substantially the same manner step 2 of Example 11.

N.M.R. ($D_2O$), δ(ppm): 1.40 (3H, d, J=7 Hz), 1.46 (3H, d, J=7 Hz), 1.80–2.64 (8H, m), 2.16 (3H, s), 4.00 (2H, s), 4.20–4.60 (3H, m), 5.01 (1H, q, J=7 Hz)

(3) Step 3

Compound (4) ⟶

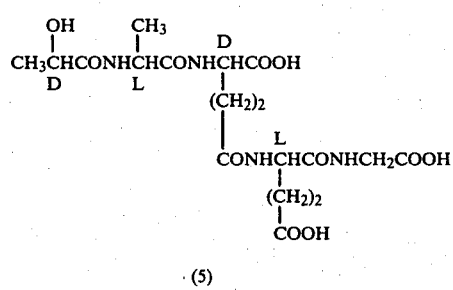

(5)

D-Lac-L-Ala-γ-D-Glu(α-OH)-L-Glu(γ-OH)-GlyOH (5) was prepared in substantially the same manner as step 2 of Example 9.

N.M.R. (D$_2$O), δ(ppm): 1.40 (3H, d, J=7 Hz), 1.46 (3H, d, J=7 Hz), 1.70–2.60 (8H, m), 4.00 (2H, s), 4.05–4.50 (4H, m)

[α]$_D$= −35.5 (c=0.2 water)

EXAMPLE 13

(1) Step 1

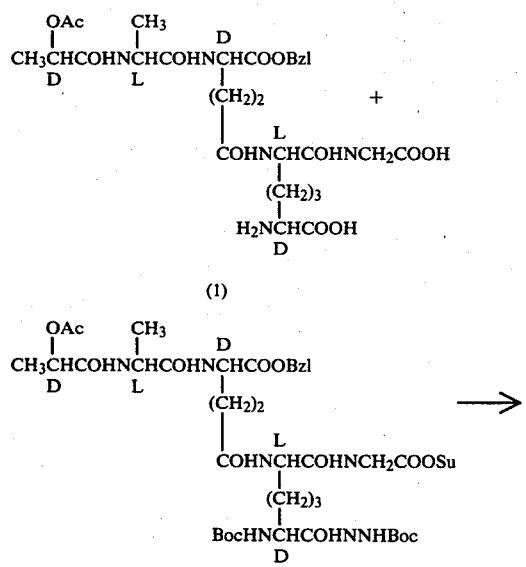

(2) Step 2

To a mixture of D-Lac(OAc)-L-Ala-γ-D-Glu(α-OBzl)-(L)-mesoDAP-(L)-GlyOH (I) (960 mg) and triethylamine (300 mg) in water (20 ml.) was added D-Lac(OAc)-L-Ala-γ-D-Glu(α-OBzl)-(L)-Boc-(D)-mesoDAP-(D)-NHNHBoc-(L)-GlyOSu (III), prepared from D-Lac-(OAc)-L-Ala-γ-D-Glu(α-OBzl)-(L)-Boc-(D)-mesoDAP-(D)-NHNHBoc-(L)-GlyOH (1.28 g), N-hydroxysuccinimid (170 mg) and bis(trimethylsilyl)acetamide (310 mg) by stirring overnight in dioxane (40 ml) at room temperature, and the mixture was stirred for 8 hours at room temperature, during which time the pH of the reaction mixture was maintained at pH 7–8 by adding triethylamine. After evaporation of dioxane, the resulting aqueous solution was washed with ethyl acetate, acidified to pH 2 with 5% hydrochloric acid and extracted with n-butanol (100 ml). The extract was concentrated and the residue was triturated with ether to give D-Lac(OAc)-L-Ala-γ-D-Glu(α-OBzl)-(L)-[D-Lac(OAc)-L-Ala-γ-D-Glu(α-OBzl)-(L)-Boc-(D)-mesoDAP-(D)-NHNHBoc-(L)-Gly]-(D)-mesoDAP-(L)-GlyOH (3) (1.78 g).

I.R. (Nujol): 3600–2200, 3260, 1720, 1640 cm$^{-1}$

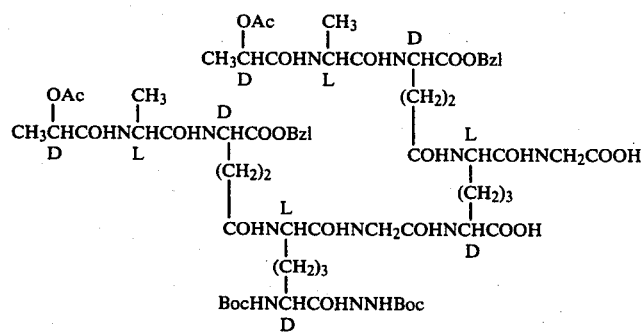

Compound (III) ⟶ 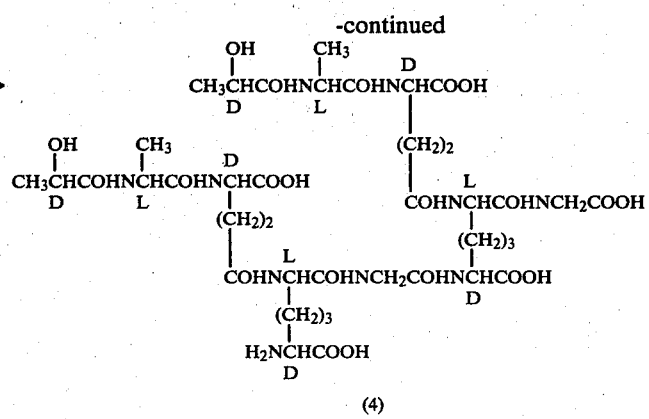

(4)

D-Lac(OAc)-L-Ala-γ-D-Glu(α-OBzl)-(L)-[D-Lac-(OAc)-L-Ala-γ-D-Glu(α-OBzl)-(L)-Boc-(D)-mesoDAP-(D)-NHNHBoc-(L)-Gly]-(D)-mesoDAP-(L)-GlyOH (3) (1.20 g) was hydrogenated over 10% palladium black (240 mg) in acetic acid (40 ml) for 3.5 hours under 2.0 atomospheric pressure of hydrogen at room temperature. After removal of the catalyst, the filtrate was evaporated. The residue was dissolved in 50% aqueous methanol (20 ml) and the solution was stirred for 2.5 hours at room temperature, maintaining the pH at 9.0 by adding 10% aqueous potassium carbonate. The solution was concentrated to about 10 ml and 1 N hydrochloric acid (10 ml) was added. To this mixture was added dropwise a solution of sodium periodate (260 mg) in water (3 ml). The mixture was stirred for 30 minutes under ice-bath cooling and then the excess reagent was decomposed with sodium bisulfite. The resulting solution was adjusted to pH 2 with 1 N sodium hydroxide and concentrated to about 10 ml. The concentrate was passed through a column packed with Hp 20 resin (20 ml) and eluted with 50% aqueous methanol. The eluate was lyophilized to give D-Lac-L-Ala-γ-D-Glu(α-OH)-(L)-[D-Lac-L-Ala-γ-D-Glu(α-OH)-(L)-mesoDAP-(D)-Gly]-(D)-mesoDAP-(L)-GlyOH (4) (0.49 g).

I.R. (Nujol): 3600–2200, 1720, 1640 cm⁻¹

N.M.R. (D$_2$O), δ(ppm): 1.3–1.5 (12H, m), 3.88 (1H, t, J=6 Hz), 4.00 (4H, s), 4.2–4.5 (1H, m)

EXAMPLE 14

(1) Step 1

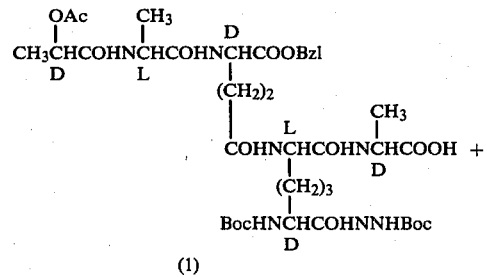 + 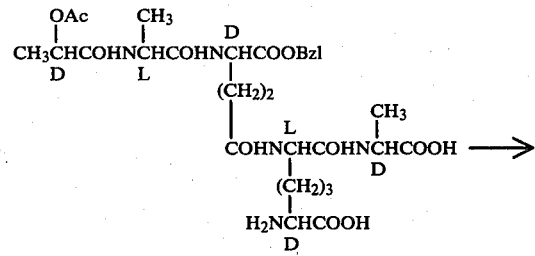 ⟶

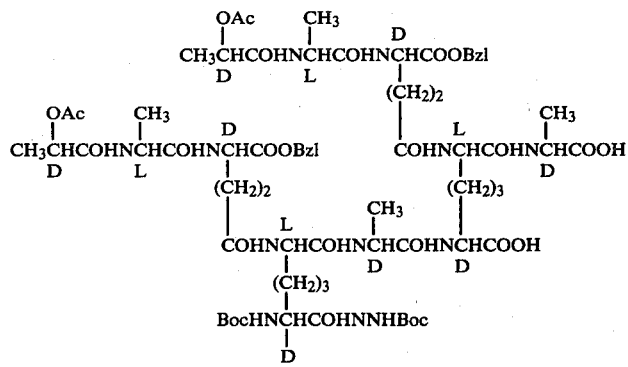

(3)

D-Lac(OAc)-L-Ala-γ-D-Glu(α-OBzl)-(L)-[D-Lac-(OAc)-L-ALa-γ-D-Glu(α-OBzl)-(L)-Boc-(D)-mesoDAP-(D)-NHNHBoc-(L)-D-Ala]-(D)-mesoDAP-(L)-D-Ala (3) was prepared in substantially the same manner as step 1 of Example 13.

I.R. (Nujol): 3250, 1720, 1640 cm⁻¹

(2) Step 2

Compound (3) ⟶ 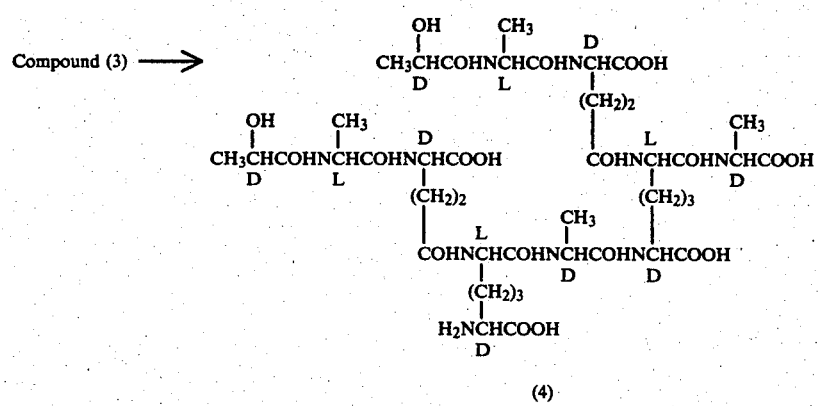

(4)

D-Lac-L-Ala-γ-D-Glu(α-OH)-(L)-[D-Lac-L-Ala-γ-D-Glu(α-OH)-(L)-mesoDAP-(L)-D-Ala]-(D)-mesoDAP-(L)-D-Ala (4) was prepared in substantially the same manner as step 2 of Example 13.

I.R. (Nujol): 3600–2200, 1720, 1660–1630 cm$^{-1}$
N.M.R. (D$_2$O), δ(ppm): 1.2–1.5 (18H, m), 3.82 (1H, t, J=6 Hz), 4.1–4.5 (11H, m)

EXAMPLE 15

(1) Step 1

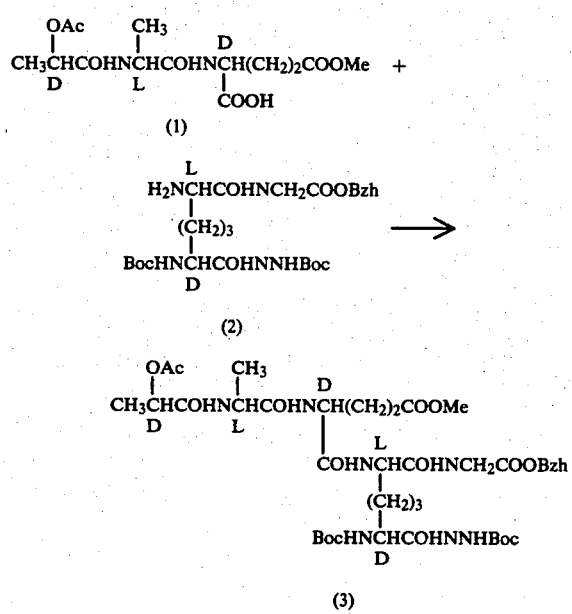

To a mixture of D-Lac(OAc)-L-Ala-D-Glu(OMe)OH (1) (310 mg) and Boc-(D)-mesoDAP-(L)-GlyOBzh-(D)-NHNHBoc (2) (560 mg) in methylene chloride (13 ml) was added N-hydroxysuccinimide (100 mg) and dicyclohexylcarbodiimide (220 mg) under ice-cooling and the mixture was stirred for an hour at the same temperature and for 14 hours at room temperature. After removal of the precipitate by filtration, the filtrate was evaporated and the residue was dissolved in ethyl acetate, washed successively with water, saturated aqueous sodium bicarbonate, brine, 2% hydrochloric acid and brine, dried over magnesium sulfate and evaporated to give an oil, which was pulverized with ether and hexane to give D-Lac(OAc)-L-Ala-α-D-Glu-(γ-OMe)-(L)-Boc-(D)-mesoDAP-(L)-GlyOBzh-(D)-NHNHBoc (3) (410 mg).

I.R. (Nujol): 3375, 1730, 1660, 1620, 1520 cm$^{-1}$
N.M.R. (CDCl$_3$), δ(ppm): 1.0–2.0 (32H, m), 2.10 (3H, s), 2.1–2.6 (2H, m), 3.67 (3H, s), 3.8–5.0 (7H, m), 5.5–5.9 (1H, m), 6.93 (1H, s), 7.33 (10H, s), 7.6–8.0 (1H, m), 8.9–9.1 (1H, m)

(2) Step 2

Compound (3) ⟶ 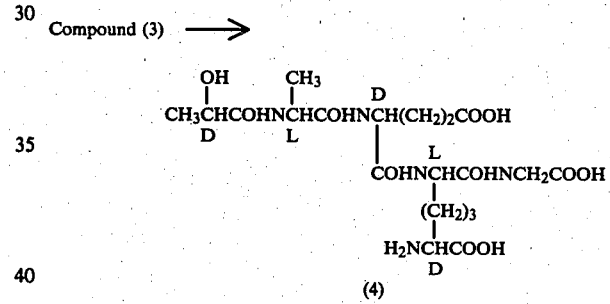

(4)

To a solution of D-Lac(OAc)-L-Ala-α-D-Glu-(γ-OMe)-(L)-Boc-(D)-mesoDAP-(L)-GlyOBzh-(D)-NHNHBoc (3) (250 mg) in methanol (1.5 ml) was added 1 N sodium hydroxide (0.6 ml) under ice-cooling and the mixture was stirred at room temperature for 45 minutes. The reaction mixture was acidified to pH 3 with 1 N hydrochloric acid (0.6 ml) and evaporated. The residue was washed with isopropylether. This residue was dissolved in trifluoroacetic acid (1 ml) and stirred for 15 minutes at room temperature. The reaction mixture was evaporated and the residue was dissolved in 1 N sulfuric acid (1 ml) and, under ice-cooling, sodium periodate (50 mg) was added. After stirring for 10 minutes, the reaction mixture was treated with 4 N sodium bisulfite until the solution was clear, neutralized to pH 3 with aqueous sodium carbonate and evaporated. The residue was dissolved in water (1 ml) and put on a column of Hp 20 (50 ml) and eluted with water. The fractions containing the object compound was evaporated and lyophyllized to give D-Lac-L-Ala-α-D-Glu(γ-OH)-(L)-mesoDAP-(L)-GlyOH (4) (110 mg).

I.R. (Nujol): 3250, 1720 (shoulder), 1640, 1520 cm$^{-1}$
N.M.R. (D$_2$O), δ(ppm): 1.36 (3H, d, J=7 Hz), 1.40 (3H, d, J=7 Hz), 1.2–1.7 (2H, m), 1.7–2.3 (6H, m), 2.3–2.6 (2H, m), 3.76 (1H, t, J=6 Hz), 3.90 (2H, s), 4.1–4.5 (4H, m)

We claim:

1. A compound of the formula or its pharmaceutically acceptable salt:

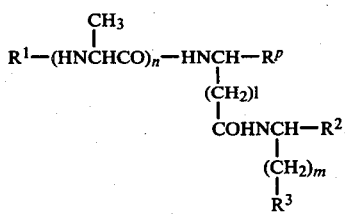

wherein
R¹ is hydrogen or acyl;
R₂ is carboxy or protected carboxy or a group of the formula: —COHN—$R_a^2$ wherein $R_a^2$ is carboxy(lower)alkyl or protected carboxy(lower)alkyl;
R³ is carboxy, protected carboxy, lower alkyl, hydroxyphenyl, carbamoyl or a group of the formula:

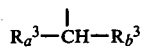

wherein $R_a^3$ is hydrogen, amino, protected amino or a cylamino, $R_b^3$ is carboxy or protected carboxy;
$R^p$ is carboxy, protected carboxy, carbamoyl, carboxy(lower)alkyl or protected carboxy(lower)alkyl;
l is an integer 2,
m is an integer 0 to 2 and
n is an integer 1,
provided that,
when $R^p$ is carbamoyl, then R¹ is acyl.

2. A compound according to claim 1, wherein R¹ is hydrogen or acyl;
R² is carboxy or a group of the formula:—CONH—$R_a^2$ wherein $R_a^2$ is carboxy(lower)alkyl;
R³ is carboxy, lower alkyl, hydroxyphenyl, carbamoyl or a group of the formula:

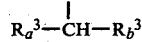

wherein $R_a^3$ is hydrogen, amino or acylamino, $R_b^3$ is carboxy;
$R^p$ is carboxy, carbamoyl or carboxy(lower)alkyl;
l is an integer 2,
m is an integer 0 to 2, and
n is an integer 1.

3. A compound according to claim 1, wherein m is an integer 0.

4. A compound according to claim 2, wherein m is 0.

5. A compound according to claim 1, wherein m is an integer 1.

6. A compound according to claim 2, wherein l is 2, m is 1.

7. A compound according to claim 1 wherein m is an integer 2.

8. A compound according to claim 2, wherein m is 2.

9. A compound according to claim 2, wherein $R^p$ is carbamoyl and R¹ is acyl.

* * * * *

UNITED STATES PATENT AND TRADEMARK OFFICE
CERTIFICATE OF CORRECTION

PATENT NO. : 4,354,966

DATED : October 19, 1982

INVENTOR(S) : KITAURA ET AL

It is certified that error appears in the above—identified patent and that said Letters Patent is hereby corrected as shown below:

On the cover page, under "Other Publications", in the line "Attorney, Agent or Firm", please delete "Olbon," and substitute therefor --Oblon,--.

In the Abstract, fourth line from the end, delete "caboxy" and substitute therefor --carboxy--.

Column 3, line 35, delete "Hetorocyclic" and substitute therefor -- Heterocyclic--.

Column 3, line 61, delete "apliphatic" and substitute therefor --aliphatic--.

Column 4, line 21, delete "aroylaklyl" and substitute therefor --aroylalkyl--.

UNITED STATES PATENT AND TRADEMARK OFFICE
CERTIFICATE OF CORRECTION

PATENT NO. : 4,354,966

DATED : October 19, 1982

INVENTOR(S) : KITAURA ET AL

It is certified that error appears in the above—identified patent and that said Letters Patent is hereby corrected as shown below:

Column 5, line 33, move ")" (first occurrence) up to the end of the previous line. (up to line 32, end).

Column 5, line 42, delete "allyoxycarbonyl" and substitute therefor --allyloxycarbonyl--.

Column 8, line 15, delete "$(HNCHCO)_N$" and substitute therefor --$(HNCHCO)_n$--.

Column 8, line 67, move "(" down to the beginning of the following line. (down to line 68, beginning).

Column 10, line 58, delete "trifluoro-acetic" and substitute therefor --trifluoroacetic--.

UNITED STATES PATENT AND TRADEMARK OFFICE
CERTIFICATE OF CORRECTION

PATENT NO. : 4,354,966

DATED : October 19, 1982

INVENTOR(S) : KITAURA ET AL

It is certified that error appears in the above—identified patent and that said Letters Patent is hereby corrected as shown below:

Column 12, line 47, delete "RP" and substitute therefor --$R^P$--.

Column 13, line 32, delete "2-(H)" and substitute therefor --2-(1H)--.

Column 15, line 67, delete "Rabey" and substitute therefor --Raney--.

Column 19, lines 58-59, delete "enchancing" and substitute therefor --enhancing--.

Column 20, line 68, delete "100" and substitute therefor --1--.

UNITED STATES PATENT AND TRADEMARK OFFICE
CERTIFICATE OF CORRECTION

PATENT NO. : 4,354,966
DATED : October 19, 1982
INVENTOR(S) : KITAURA ET AL

It is certified that error appears in the above—identified patent and that said Letters Patent is hereby corrected as shown below:

Column 22, line 10, delete "intriplicate" and substitute therefor --in triplicate--.

Column 22, line 26, delete "thymedine" and substitute therefor --thymidine--.

Column 23, line 11 (in Notes to Table 4), delete "Ovalbumun" and substitute therefor --Ovalbumin--.

Column 23, line 29, delete "collidal" and substitute therefor --colloidal--.

Column 24, line 24, delete "mangesium" and substitute therefor --magnesium--.

UNITED STATES PATENT AND TRADEMARK OFFICE
CERTIFICATE OF CORRECTION

PATENT NO. : 4,354,966

DATED : October 19, 1982

INVENTOR(S) : KITAURA ET AL

It is certified that error appears in the above—identified patent and that said Letters Patent is hereby corrected as shown below:

Column 29, line 19, delete "distroyed" and substitute therefor --destroyed--.

Column 32, line 68, delete "(" (parenthesis) before "20".

Column 33, line 34, after "-OBzl)", add an additional ")".

Column 33, , line 59, after "-OH), add an additional ")".

Column 39, line 54 in Example 8, delete "$CH_2)_2$" and substitute therefor --$(CH_2)_2$--.

UNITED STATES PATENT AND TRADEMARK OFFICE
CERTIFICATE OF CORRECTION

PATENT NO. : 4,354,966

DATED : October 19, 1982

INVENTOR(S) : KITAURA ET AL

It is certified that error appears in the above—identified patent and that said Letters Patent is hereby corrected as shown below:

Column 40, line 56, delete "throughly" and substitute therefor --thoroughly--.

Column 41, line 52, in Example 10, delete "bzl" and substitute therefor --Bzl--.

Column 43, line 50, after "solution was", insert --added--.

Column 44, line 62, between "ner" and "step", insert --as--.

Column 45, bottom-"(2) Step 2" should be at the bottom of Column 46.

UNITED STATES PATENT AND TRADEMARK OFFICE
CERTIFICATE OF CORRECTION

PATENT NO. : 4,354,966

DATED : October 19, 1982

INVENTOR(S) : KITAURA ET AL

It is certified that error appears in the above—identified patent and that said Letters Patent is hereby corrected as shown below:

Column 46, line 8, delete "hydroxysuccinimid" and substitute therefor --hydroxysuccinimide--.

Column 47, line 23, delete "atomospheric" and substitute therefor --atmospheric--.

Column 47, bottom-- "(2) Step 2" should be at the bottom of Column 48.

Column 48, last line of Example 14, delete the line between "C" (second to last line) and "D" (last line).

Column 48, line 61, delete "-ALa" and substitute therefor -- -Ala--.

UNITED STATES PATENT AND TRADEMARK OFFICE
CERTIFICATE OF CORRECTION

PATENT NO. : 4,354,966
DATED : October 19, 1982
INVENTOR(S) : KITAURA ET AL

It is certified that error appears in the above—identified patent and that said Letters Patent is hereby corrected as shown below:

Column 51, line 29, delete "or a cylamino," and substitute therefor --or acylamino,--.

Column 52, line 26, delete "1 is 2,".

Signed and Sealed this

Sixth Day of September 1983

[SEAL]

Attest:

Attesting Officer

GERALD J. MOSSINGHOFF

Commissioner of Patents and Trademarks